United States Patent
Galbo et al.

(10) Patent No.: US 7,390,904 B2
(45) Date of Patent: Jun. 24, 2008

(54) HYDROGEN PEROXIDE CATALYZED PROCESS FOR THE PREPARATION OF STERICALLY HINDERED N-HYDROCARBYLOXYAMINES

(75) Inventors: James P. Galbo, Wingdale, NY (US); Robert E. Detlefsen, Putnam Valley, NY (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 589 days.

(21) Appl. No.: 10/889,339

(22) Filed: Jul. 12, 2004

(65) Prior Publication Data

US 2005/0014948 A1    Jan. 20, 2005

Related U.S. Application Data

(60) Provisional application No. 60/486,994, filed on Jul. 14, 2003.

(51) Int. Cl.
*C07D 401/12*    (2006.01)
*C07D 211/22*    (2006.01)

(52) U.S. Cl. .................. 546/184; 546/216; 546/240

(58) Field of Classification Search .............. 546/184, 546/188, 216, 240
See application file for complete search history.

(56) References Cited

U.S. PATENT DOCUMENTS

| | | | |
|---|---|---|---|
| 3,970,660 A * | 7/1976 | Bollyky ............... 546/261 |
| 4,831,134 A | 5/1989 | Winter et al. ............ 540/524 |
| 4,921,962 A * | 5/1990 | Galbo et al. ............. 546/184 |
| 4,961,962 A | 10/1990 | Morimoto ............... 427/180 |
| 5,021,577 A | 6/1991 | Galbo .................... 546/188 |
| 5,204,473 A | 4/1993 | Winter et al. ........... 546/188 |
| 5,374,729 A | 12/1994 | Galbo .................... 546/242 |
| 5,629,426 A | 5/1997 | Pastor et al. ............ 546/216 |
| 5,654,434 A | 8/1997 | Pastor et al. ............ 546/242 |
| 5,777,126 A | 7/1998 | Pastor et al. ............ 546/244 |
| 6,166,212 A * | 12/2000 | Galbo et al. ............ 546/216 |
| 6,211,378 B1 | 4/2001 | Babiarz et al. .......... 546/242 |
| 6,271,382 B1 * | 8/2001 | Iwazaki ................. 546/184 |
| 6,638,997 B2 * | 10/2003 | Galbo et al. ............. 524/99 |
| 6,900,328 B2 * | 5/2005 | Hafner et al. ........... 546/216 |
| 2005/0256312 A1 * | 11/2005 | Osterholt et al. ......... 546/16 |

OTHER PUBLICATIONS

Galbo et al. "Process for preparing . . . " CA 113:152265 (1990).*
D. H. R. Barton et al., Tetrahedron, (1996), vol. 52, Issue 31, pp. 10301-10312.
Yoshioka et al., Bull. Chem. Soc. Japan, (1972), vol. 45, pp. 636-638.
Rauckman et al., Synthetic Communications, (1975), vol. 5, pp. 409-413.

* cited by examiner

*Primary Examiner*—Celia Chang
(74) *Attorney, Agent, or Firm*—Tyler A. Stevenson; Mervin G. Wood; Joseph Suhadolnik

(57) ABSTRACT

Sterically hindered N-hydrocarbyloxyamines are prepared from hindered amine N-oxyl compounds by a process which uses hydrogen peroxide or a hydrogen peroxide equivalent, a catalytic amount of a peroxide decomposing transition metal salt, metal oxide, or metal-ligand complex, a hydrocarbon solvent containing no activated hydrogen atoms, and a relatively inert cosolvent. These compounds are useful as thermal and light stabilizers for a variety of organic substrates.

29 Claims, No Drawings

HYDROGEN PEROXIDE CATALYZED PROCESS FOR THE PREPARATION OF STERICALLY HINDERED N-HYDROCARBYLOXYAMINES

This application claims benefit under 35 USC 119(e) of U.S. provisional application No. 60/486,994, filed Jul. 14, 2003.

This invention pertains to a process for preparing sterically hindered N-hydrocarbyloxyamines which uses hydrogen peroxide or a hydrogen peroxide equivalent, a catalytic amount of a peroxide decomposing transition metal salt, metal oxide, or metal-ligand complex, a hydrocarbon solvent containing no activated hydrogen atoms, and a relatively inert cosolvent. These compounds are useful as thermal and light stabilizers for a variety of organic substrates.

BACKGROUND OF THE INVENTION

U.S. Pat. No. 4,921,962 claims a process for the formation of N-hydrocarbyloxy derivatives of sterically hindered amines in which a hindered amine or N-oxyl substituted hindered amine is reacted with a hydrocarbon solvent in the presence of a hydroperoxide and a metal carbonyl, metal oxide or metal alkoxide catalyst.

U.S. Pat. No. 5,374,729 describes a process for the preparation of N-methoxy derivatives of sterically hindered amines from the reaction of hindered amine N-oxyl compounds with methyl radicals produced by the combination of aqueous hydrogen peroxide and a peroxide-decomposing transition metal salt in the presence of dimethyl sulfoxide.

D. H. R. Barton, et al., in *Tetrahedron*, 1996, 52, 10301-12, describe the formation of N-alkoxy substituted sterically hindered amine derivatives obtained by the reaction of unactivated hydrocarbons with iron(II) and iron(III) salts or metal-ligand complexes, hydrogen peroxide, and pyridine/acetic acid or pyridine/picolinic acid in the presence of 1-oxyl-2,2,6,6-tetramethylpiperidine (TEMPO).

U.S. Pat. No. 6,166,212 claims a process in which an N-oxyl compound is reacted with a peroxide or organic hydroperoxide and a catalytic amount of a metal salt or metal-ligand complex in an alcohol solvent to synthesize N-hydroxyalkoxy substituted hindered amine stabilizer molecules.

U.S. Pat. No. 6,211,378 teaches an environmentally friendly process for the preparation of 4-functionalized sterically hindered N-hydrocarbyloxyamine derivatives of 2,2,6,6-tetramethylpiperidines using hydrogen peroxide to oxidize a hindered amine to an N-oxyl compound which is reacted with one equivalent of a compound having an allylic, benzylic, or activated methine hydrogen.

U.S. Pat. Nos. 5,629,426, 5,654,434, and 5,777,126 disclose a process for the formation of N-oxyl sterically hindered amines from hindered amines using aqueous hydrogen peroxide.

N-hydrocarbyloxy derivatives of 2,2,6,6-tetramethylpiperidines can be made in a variety of ways, which include the following: a) catalytic hydrogenation of an N-oxyl hindered amine to form a hydroxylamine, as taught in U.S. Pat. No. 4,831,134, followed by alkylation of the hydroxylamine using a strong base such as sodium hydride and an alkyl halide, as taught in U.S. Pat. No. 5,204,473; b) reaction of 2 equivalents of N-oxyl hindered amine with tributyltin hydride and an iodo- or bromo-substituted hydrocarbon in an inert solvent such as chlorobenzene, as taught in U.S. Pat. No. 5,021,577; c) heating a solution of an organic peroxide, such as di-tert-butyl peroxide, an N-oxyl compound, and a hydrocarbon with abstractable hydrogen atoms as disclosed in U.S. Pat. No. 5,204,473; d) heating a mixture of an N-oxyl hindered amine, an organic hydroperoxide, a catalytic amount of a molybdenum catalyst, and a hydrocarbon solvent with abstractable hydrogen atoms as taught in U.S. Pat. No. 4,921,962; and e) reaction of a mixture of iron(II) perchlorate or iron(III) chloride, hydrogen peroxide, acetic acid or picolinic acid, adamantane or cyclohexane and an excess of pyridine solvent in the presence of N-oxyl-2,2,6,6-tetramethylpiperidine (TEMPO), as disclosed by Barton, et al., in *Tetrahedron*, 1996, 52, 10301-12.

The instant process involves the formation of N-hydrocarbyloxy hindered amine derivatives by reacting a mixture of an N-oxyl hindered amine with hydrogen peroxide and a catalytic amount of metal salt, oxide, or metal ligand complex, and where needed, a mineral acid or organic acid, in the presence of a hydrocarbon and a cosolvent.

The instant process does not require specialized reagents such as alkyl halides, sodium hydride, or tributyltin hydride. The instant process offers the advantage of using hydrogen peroxide instead of a more expensive tertiary alkyl hydroperoxide. Furthermore, the by-product from hydrogen peroxide is water, whereas tertiary alkyl hydroperoxides produce alcohol by-products, such as t-butyl alcohol from t-butyl hydroperoxide. These alcohols must be separated from the desired reaction product and disposed of. Products made from solvents which boil near or below 100° C., such as cyclohexane and heptane, are most efficiently made by carrying out the reactions in a pressure vessel in order to obtain the desired 100-150 degree reaction temperature. The instant process does not require a pressure vessel for lower boiling hydrocarbon solvents. For example, reactions with cyclohexane can be effectively carried out at 60° C. The use of lower reaction temperatures in the instant process requires less energy and eliminates safety issues specifically associated with the use of pressure vessels.

The instant process does not require the use of substantial amounts of toxic solvents, like pyridine. In addition to its toxicity, pyridine is difficult to remove from the reaction mixture because of its relatively high boiling point, 115° Celsius. Barton, et al., remove pyridine by an acid work-up involving concentrated sulfuric acid and ice. The instant process obtains excellent yields of N-hydrocarbyloxy products with methanol (bp 65°) or acetonitrile (bp 81°) as a cosolvent. These materials are easy to remove by a solvent strip or simple distillation and have the advantage of being water-soluble.

The instant process does not require the addition of additives such as ascorbic acid or zinc.

The instant invention, though primarily concerned with the formation of N-hydrocarbyloxy amines from their N-oxyl precursors, also teaches a two-step process in which a hindered amine is oxidized to the intermediate N-oxyl compound. The N-oxyl compound is not isolated prior to conversion to the N-hydrocarbyloxyamine. Hydrogen peroxide is an inexpensive and efficient reagent for such an oxidation.

U.S. Pat. Nos. 5,629,426, 5,654,434, and 5,777,126 disclose a process for the formation of N-oxyl sterically hindered amines from hindered amines using aqueous hydrogen peroxide, a metal passivator, an ammonium or alkali carbonate or bicarbonate, and water as the solvent.

Published methodologies for the oxidation of hindered amines to N-oxyl compounds using hydrogen peroxide and sodium tungstate are described by Yoshioka, et al., in *Bull. Chem. Soc.* Japan, 1972, 45, 636-638 and Rauckman, et al., in *Synthetic Communications,* 1975, 5, 409-413.

U.S. Pat. No. 4,961,962 teaches the conversion of hindered amines to N-hydrocarbyloxy derivatives, without isolation of the intermediate N-oxyl compound, using organic hydroperoxides.

The instant invention provides an improved process for the preparation of sterically hindered N-hydrocarbyloxyamines.

DETAILED DISCLOSURE

The instant invention pertains to a process for preparing sterically hindered N-hydrocarbyloxyamines of formula I

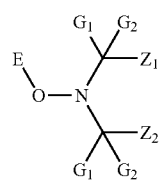

(I)

which process comprises
reacting a sterically hindered nitroxyl compound of formula II

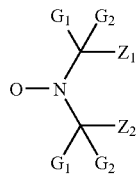

(II)

with a hydrocarbon containing no activated hydrogen atoms
in the presence of hydrogen peroxide or a hydrogen peroxide equivalent, a catalytic amount of a peroxide decomposing transition metal salt, metal oxide, or metal-ligand complex, and a relatively inert cosolvent,
at a suitable temperature for a suitable time which brings about the desired conversion, wherein
$G_1$ and $G_2$ are independently alkyl of 1 to 4 carbon atoms or are together pentamethylene,
$Z_1$ and $Z_2$ are each methyl, or $Z_1$ and $Z_2$ together form a linking moiety which may additionally be substituted by an ester, ether, amide, amino, carboxy or urethane group, and
E is $C_5$-$C_{18}$ alkyl, $C_5$-$C_{12}$ cycloalkyl, or $C_7$-$C_{12}$ bicycloalkyl; or E is $C_{10}$-$C_{20}$ aralkyl or aralkyl substituted by alkyl or aryl,
with the proviso that in the hydrocarbon, no carbon atom attached to an aromatic ring is substituted by hydrogen.

The group E is derived from the hydrocarbon to form the hydrocarbyloxy group. When $Z_1$ and $Z_2$ together form a linking moiety as described above, the structure of the linking moiety is not critical to the instant process, except that the moiety formed by $Z_1$ and $Z_2$ should be essentially inert to the reaction conditions. The structure of the linking moiety formed by $Z_1$ and $Z_2$ together may be such that the compound of formula (I) has more than one N-hydrocarbyloxy group, such as the diester of Instant Example 4. The choice of $Z_1$ and $Z_2$ is usually governed by the intended use of the N-hydrocarbyloxy reaction product.

For example, the instant invention pertains to a process for preparing sterically hindered N-hydrocarbyloxyamines of formula Ia

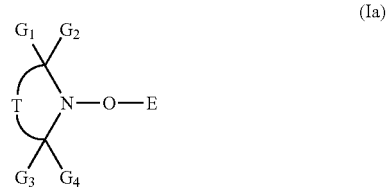

(Ia)

which process comprises
reacting a sterically hindered nitroxyl compound of formula IIa

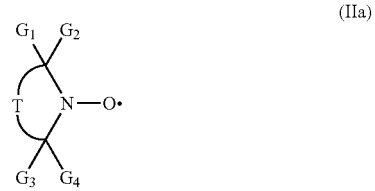

(IIa)

with a hydrocarbon containing no activated hydrogen atoms
in the presence of hydrogen peroxide or a hydrogen peroxide equivalent, a catalytic amount of a peroxide decomposing transition metal salt, metal oxide, or metal-ligand complex, and a relatively inert cosolvent,
at a suitable temperature for a suitable time which brings about the desired conversion,
wherein $G_1$ through $G_4$ are each $C_1$-$C_4$ alkyl, or $G_1$ and $G_2$ together are pentamethylene, or $G_1$-$G_2$ together and $G_3$-$G_4$ together are each pentamethylene,
T is a divalent organic radical required to complete a five, six, or seven membered ring containing the hindered amine nitrogen and the two quaternary carbon atoms substituted by $G_1$ through $G_4$, with the understanding that the five, six, or seven membered ring formed by T may contain oxygen, a lactone —C(=O)—O—, a lactam —NR1-C(=O)—, where R1 is hydrogen or $C_1$-$C_8$ alkyl or, for six membered rings, the group —C(=O)—NR1-C(=O)—, or
T is alkylene of 2 to 4 carbon atoms substituted by X,
X is hydrogen, hydroxyl, oxo, —NH—CO—R2, —O—CO—R2, or —NH—CO—NH—R2, where R2 is alkyl of 1 to 18 carbon atoms, and E is $C_5$-$C_{18}$ alkyl, $C_5$-$C_{12}$ cycloalkyl, or $C_7$-$C_{12}$ bicycloalkyl. E may also be $C_{10}$-$C_{20}$ aralkyl or aralkyl substituted by alkyl or aryl, with the proviso that in the hydrocarbon, no carbon atom attached to an aromatic ring is substituted by hydrogen.

The group E is derived from the hydrocarbon to form the hydrocarbyloxy group.

For example, the instant process involves the preparation of a compound of formula (Ib)

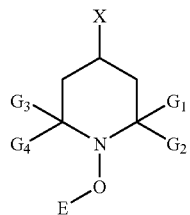

(Ib)

which process comprises
reacting a sterically hindered nitroxyl compound of formula IIb

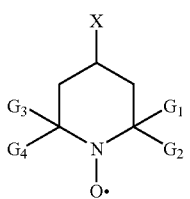

(IIb)

with a hydrocarbon containing no activated hydrogen atoms
in the presence of hydrogen peroxide or a hydrogen peroxide equivalent, a catalytic amount of a peroxide decomposing transition metal, metal salt, metal oxide, or metal-ligand complex, and a relatively inert cosolvent,
at a suitable temperature for a suitable time which brings about the desired conversion,
wherein $G_1$-$G_4$ and X have the meanings described previously, and with the proviso that in the hydrocarbon, no carbon atom attached to an aromatic ring is substituted by hydrogen.

For example, the instant process involves the preparation of a compound of formula (Ic)

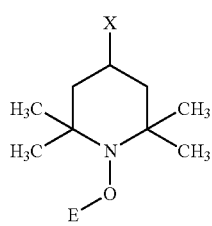

(Ic)

which process comprises
reacting a sterically hindered nitroxyl compound of formula IIc

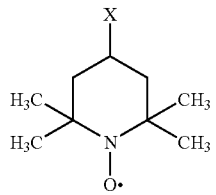

(IIc)

with a hydrocarbon containing no activated hydrogen atoms
in the presence of hydrogen peroxide or a hydrogen peroxide equivalent, a catalytic amount of a peroxide decomposing transition metal, metal salt, metal oxide, or metal-ligand complex, and an inert or relatively inert cosolvent,
at a suitable temperature for a suitable time which brings about the desired conversion,
where E is hexyl, heptyl, octyl, or cyclohexyl, and
X is hydrogen, hydroxyl, oxo, —O—CO—R2, wherein R2 is 1 to 8 carbon atoms.

Examples of the hydrocarbons containing no activated hydrogen atoms for the instant process are hexane, heptane, octane, nonane, decane, dodecane, 2,2,4-trimethylpentane (isooctane), octadecane, cyclopentane, cyclohexane, cyclooctane, cyclododecane, methylcyclohexane, norbornane, decahydronaphthalene (decalin), dicyclohexyl, tert-butylbenzene, 1,4-di-tert-butylbenzene, 4,4'-di-tert-butylbiphenyl, and 2,2-diphenylpropane. Although the hydrocarbon is a reactant, excess hydrocarbon is typically used as a solvent for the instant process. Furthermore, the use of excess hydrocarbon reduces the possibility that more than one N-oxyl moiety will bind to the same solvent molecule to form higher molecular weight materials. Although these higher molecular weight compounds would be expected to be active polymer stabilizer molecules, such compounds may have different physical properties than the compounds of formula (I). A mixture of N-hydrocarbyloxy products may result if the hydrocarbon used in the instant process has non-equivalent hydrogen atoms. For example, cyclohexane can give only one product whereas hexane can give up to three distinct products.

The present hydrocarbon is for example hexane, heptane, octane, or cyclohexane.

The amount of hydrocarbon for the instant process is for example about 1 to about 15 moles of hydrocarbon per mole of N-oxyl moiety. For example, the amount of about 2 to about 10 moles of hydrocarbon per mole of N-oxyl moiety is effective. For instance, the amount of hydrocarbon is about 5 to about 10 moles per mole of N-oxyl moiety.

The amount of hydrogen peroxide or hydrogen peroxide equivalent is for example about 1 to about 10 moles per mole of N-oxyl moiety. For example the amount of hydrogen peroxide or hydrogen peroxide equivalent is about 2 to about 5 moles of hydrogen peroxide per mole of N-oxyl moiety.

Hydrogen peroxide or hydrogen peroxide equivalent is used for instance at about 15% to about 50% concentration aqueous solution based on weight. This is the concentration of the hydrogen peroxide or hydrogen peroxide equivalent that is employed for the reaction. For instance, the concentration is about 30% to about 50% hydrogen peroxide or hydrogen peroxide equivalent based on weight. For example, the concentration of hydrogen peroxide or hydrogen peroxide equivalent is about 50% aqueous solution based on weight.

The N-oxyl hindered amines of formula (II) may be prepared for example from reaction of the corresponding hindered amine with hydrogen peroxide and sodium tungstate as described by E. G. Rozantsev and V. D. Sholle in *Synthesis*, 1971, 190-202, with hydrogen peroxide and an ammonium or alkali carbonate or bicarbonate catalyst as taught in U.S. Pat. Nos. 5,629,426 and 5,777,126, with hydrogen peroxide in the absence of any catalyst as taught in U.S. Pat. No. 5,654,434, or with t-butyl hydroperoxide and a molybdenum catalyst as taught in U.S. Pat. No. 4,691,015. The relevant disclosures of these U.S. Patents are hereby incorporated by reference.

For instance, the instant process involves the reaction of an N-oxyl compound of formula (II) with a mixture of about 1 to about 40 moles of a hydrocarbon containing no allylic or benzylic hydrogen atoms, about 0.1 to about 10 parts of a relatively inert cosolvent per part of hydrocarbon, about 1 to about 10 moles of hydrogen peroxide or a hydrogen peroxide equivalent, and about 0.0005 to about 0.1 moles of a transition metal salt, oxide, or metal-ligand complex, with all quantities calculated per mole of N-oxyl moiety.

The instant process is carried out for example at a temperature between about 0 degrees and about 100 degrees Celsius. For instance, the process is carried out at a temperature of about 20 degrees to about 100 degrees or from about 50 degrees to about 100 degrees Celsius.

When T is —$CH_2CH(OH)CH_2$— or —$CH_2C(=O)CH_2$—, the compounds of formula (I) are also simple building blocks that can be readily elaborated into more complex higher molecular weight N-hydrocarbyloxy hindered amines using well known chemical reactions including transesterification and reductive amination.

The cosolvent is for example methanol or acetonitrile.

The cosolvent improves the miscibility of the hydrocarbon and hydrogen peroxide, which is used for example as about a 15% to about a 50% aqueous solution based on weight, in the reaction medium. An ideal cosolvent is inert to the reaction conditions of the instant process. If the cosolvent is not completely inert, any resulting by-products should be easily removed from the desired product, or if they are not removed, such by-products should not adversely affect the performance of the product in its end use. The cosolvent should also be relatively easy to remove from the reaction mixture, such as by a water wash, simple distillation, or solvent strip. An effective cosolvent for the instant process is methanol. In order to improve the solubility of the metal in the reaction medium, a small amount of water may be added to the reaction mixture. Water is not considered to be a cosolvent in the instant process.

The term relatively inert is defined as the cosolvent reacting with the N-oxyl compound, under the reaction conditions, to the extent that no more than about 5-10 mole percent of the N-oxyl compound forms a reaction product with the cosolvent.

The quantity of cosolvent used is for example from about 0.5 to about 2 parts based on 1 part of hydrocarbon by volume.

The instant process uses a less than stoichiometric amount, based on peroxide, of a transition metal, which reacts with hydrogen peroxide. Effective metals include vanadium(II), vanadium (III), tin(IV), copper(I), copper(II), titanium(III), titanium(IV), manganese(II), manganese(III), iron(II), iron (III), cerium (III), cobalt(II), and ruthenium(III). The metal may be introduced into the reaction in the form of a salt. The transition metal salt are defined a salts of the above metals with counterions, which counterions are for example chloride, sulfate, acetate, pivalate (trimethylacetate), acetylacetonate (acac), citrate, oxalate, nitrate, perchlorate, trifluoroacetate, methanesulfonate, trifluoromethanesulfonate, para-toluenesulfonate, tetrafluoroborate, ethylenediammonium sulfate, hexafluorophosphate, cyanide, oxide, or hydroxide.

Metal salts or oxides are for example iron(II) chloride, iron(III) chloride, iron(III) acetylacetonate, iron(II) sulfate, iron(III) sulfate, iron(II) acetate, iron(II) oxide, iron(III)oxide, iron (II,III) oxide, iron(III) citrate, iron(II) oxalate, iron (III) oxalate, iron(III) nitrate, iron(II) perchlorate, iron(III) perchlorate, iron(II) trifluoroacetate, iron(II) tetrafluoroborate, iron(II) ethylenediammonium sulfate, iron(III) para-toluenesulfonate, ferrocenium hexafluorophosphate, ferrocenium tetrafluoroborate, copper(I) chloride, copper(II) chloride, copper(II) sulfate, copper(II) trifluoromethanesulfonate, or copper(II) trifluoroacetate. For example, metal salts copper(I) chloride, copper(II) chloride, copper(II) sulfate, iron(II) chloride, iron(II) sulfate, iron(III) sulfate, or iron(III) chloride.

The metal may be introduced into the reaction mixture in a finely divided state such as iron or copper powder or nano-sized activated iron or copper powder.

The metal may also be complexed with a ligand such as 2,2'-dipyridyl, ethylenediaminetetraacetic acid or its disodium salt, triphenylphosphine oxide, cyclopentadiene, the anion of acetylacetone, or the reaction product of salicylaldeyhde or alkyl substituted salicylaldehyde with a 1,2-diamine. Examples of effective metals used for metal-ligand complexes in the instant process include: vanadium(II), vanadium (III), tin(IV), copper(I), copper(II), titanium(III), titanium(IV), manganese(II), manganese(III), iron(II), iron(III), cerium (III), cobalt(II), and ruthenium(III). Metal ligand complexes may be purchased commercially or formed in situ by mixing a metal salt with the ligand. The amount of ligand may be less than the amount required to completely complex the metal based on its oxidation state. The metal salt or metal-ligand complex may be bound to a solid support such as silica gel so that the catalyst can be recovered and used again. More specifically, ligands for the above metals include 2,2'-dipyridyl, 2,2':6,2"-terpyridine, 2,3-bis(2-pyridyl)pyrazine, 1,10-phenanthroline, ethylenediaminetetraacetic acid, ethylenediaminetetraacetic acid disodium salt, triphenylphosphine oxide, pyridine, picolinic acid, 2-pyrazinecarboxylic acid, diimines formed from the reaction of aniline or substituted anilines with 1,2-diketones such as 2,3-butanedione, diimines such as N,N'-bis(salicylidene)ethylenediamine or N,N'-bis(3,5-di-tert-butylsalicylidene)-1,2-cyclohexanediamine, formed from the reaction of 1,2-diamines with salicylaldehyde or alkyl or dialkyl substituted salicylaldehydes, and in the case of iron, cyclopentadiene (ferrocenium salts). 2,2'-Dipyridyl is a metal ligand that is effective.

The metal may be in the form of a metal-ligand complex such as are ferrocenium [dicyclopentadienyliron(I)] or those metal-ligand complexes made from iron(II), iron(III), copper (I), or copper(II) salts and 2,2'-dipyridyl, triphenylphosphine oxide, ethylenediaminetetraacetic acid, or ethylenediamine-tetraacetic acid disodium salt. Metal-ligand complexes are for example those made from iron(II) chloride, iron(II) chloride, iron(II) sulfate, or iron(III) sulfate and 2,2'-dipyridyl.

The amount of metal salt, oxide, or metal-ligand complex is for example about 0.001 to about 0.1 moles per mole of N-oxyl moiety. For instance, the amount of metal salt, oxide or metal-ligand complex is from about 0.002 to about 0.05 moles per mole of N-oxyl.

The instant process may optionally contain an acid. An inorganic acid or a carboxylic, sulfonic, phosphonic, or phosphinic acid is often added to the reaction mixture in an amount corresponding to up to about one mole of acid per mole of N-oxyl moiety. The addition of acid may improve the solubility and efficiency of the metal catalyst in the reaction medium. The acid is for example hydrochloric acid, sulfuric acid, phosphoric acid, trifluoroacetic acid, tetrafluoroboric acid, acetic acid, chloroacetic acid, dichloroacetic acid, trichloroacetic acid, boric acid, citric acid, or methanesulfonic acid. When acid is used in the instant process, the amount of acid is for example about 0.005 to about 1 mole per mole of N-oxyl moiety, for example, from about 0.02 to about 0.25 moles of acid per mole of N-oxyl moiety. It is possible in certain instances to obtain excellent yields of N-hydrocarbyloxy products without the addition of acid to the reaction mixture.

Up to about 5 mole percent of a quaternary ammonium salt, such as tetrabutylammonium hydrogen sulfate or tetrabutylammonium chloride, may be added to the reaction mixture. The use of a quaternary ammonium salt does not eliminate the use of the cosolvent.

The instant process may be run in the presence of air or in an inert atmosphere such as nitrogen or argon.

A hydrogen peroxide equivalent such as urea hydrogen peroxide may be used in the instant process.

In the instant process, a solution of aqueous hydrogen peroxide is slowly added to a mixture of the N-oxyl compound, a metal salt, oxide or metal-ligand complex, acid if used, the hydrocarbon, and cosolvent, which has been brought to the desired temperature for reaction. The proper temperature is maintained by controlling the rate of peroxide addition and/or using a heating or cooling bath. After the peroxide is added, the reaction mixture is stirred until the starting N-oxyl compound is no longer present or is no longer being converted to product. The reaction is best monitored by thin layer chromatography, gas chromatography, or liquid chromatography. Additional portions of the metal salt or metal-ligand complex can be added while the reaction is in progress. After the initial peroxide has been charged to the reaction mixture, more peroxide can be added dropwise to complete the reaction.

A variation of the instant process is to simultaneously add separate solutions of the peroxide and the N-oxyl compound to a mixture of the hydrocarbon, cosolvent, acid if used, and metal salt, oxide or metal-ligand complex. The N-oxyl compound may be dissolved in water, the hydrocarbon solvent, or the cosolvent used in the reaction. Some of the N-oxyl compound may be introduced into the reaction mixture prior to starting the peroxide addition, and all of the N-oxyl compound should be added prior to completing the peroxide addition.

Another variation of the instant process is to simultaneously add separate solutions of the peroxide and the metal salt, oxide, or metal-ligand complex simultaneously to a mixture of the N-oxyl compound, hydrocarbon, cosolvent, and acid if used. The metal may be dissolved in water, water plus acid, or the hydrocarbon and/or cosolvent. Some of the metal solution may be introduced into the reaction mixture prior to starting the peroxide addition.

Another variation of the instant process is to simultaneously add separate solutions of the peroxide, the N-oxyl compound, and the metal salt, oxide, or metal-ligand complex to a mixture of the hydrocarbon, cosolvent, and acid if used. A portion of the N-oxyl compound and/or the metal may be introduced into the reaction mixture prior to starting the peroxide addition, and all of the N-oxyl compound should be added prior to completing the peroxide addition.

Acid may be added in one portion at the beginning of the reaction, or a portion of acid may be added at the beginning of the reaction and the remainder added while the reaction is in progress. Some or all of the acid may be mixed with the metal salt before it is added to the reaction mixture.

If a metal-ligand complex is prepared in situ, the metal salt and ligand are most effectively mixed prior to contact with the N-oxyl compound.

A convenient modification of the instant process is to start with the hindered amine of formula (III), which is the precursor of N-oxyl compound (II). The amine is oxidized to the corresponding N-oxyl compound using hydrogen peroxide. The N-oxyl compound is subsequently converted without isolation to the product of formula (I) using the process already described.

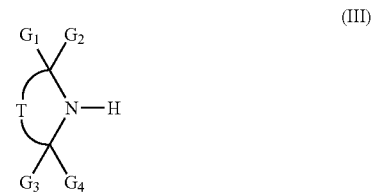

(III)

For instance, about 1.5 to about 3 moles of an about 30% to about 50% aqueous hydrogen peroxide or a hydrogen peroxide equivalent, per mole of hindered amine moiety, are added to a mixture of hindered amine, about 0.005 to about 0.05 moles (about 0.5 to about 5 mole percent) of an ammonium or alkali metal carbonate or bicarbonate salt, and methanol or acetonitrile at a temperature of about 50 to about 80° C. A small amount of water may be used to aid in dissolving the metal catalyst. If the hindered amine of formula (3) is not sufficiently soluble in the reaction medium, the hydrocarbon solvent used in the subsequent formation of the N-hydrocarbyloxy product may be added to the reaction mixture. Alternatively, the oxidation may be conveniently performed at form about 20 to about 40° C. in methanol or acetonitrile solvent using about 1.5 to about 3 moles of aqueous hydrogen peroxide, about 0.005 to about 0.05 moles of an ammonium or alkali metal carbonate or bicarbonate and about 0.001 to about 0.05 moles of sodium tungstate or a suitable substitute. A small amount of water may be used to aid in dissolving the metal catalysts.

Upon completion of the oxidation reaction, the appropriate amount of hydrocarbon solvent and cosolvent are added to the reaction mixture containing the crude N-oxyl compound. According to the process already described for the conversion of the compound of formula (II) to the product of formula (I), an aqueous solution of a metal salt, oxide or metal-ligand complex, and acid, if desired, are added to the hydrocarbon-cosolvent mixture that contains the N-oxyl compound. After this mixture is brought to the desired temperature for reaction, aqueous hydrogen peroxide is slowly added to bring about the conversion of the N-oxyl compound (IIa) to the N-hydrocarbyloxy product of formula (I). Where possible, the water from the oxidation reaction is separated from the reaction mixture and discarded after it is extracted with cosolvent and/or the appropriate hydrocarbon solvent. Care should be taken when introducing the metal catalyst for conversion of the N-oxyl intermediate to the N-hydrocarbyloxy compound, because unreacted peroxide may be present in the reaction mixture.

Illustrative of the sterically hindered N-hydrocarbyloxyamines prepared by the instant process are:
Bis(1-cyclohexyloxy-2,2,6,6-tetramethylpiperidin-4-yl) sebacate
1-Cyclohexyloxy-4-methoxy-2,2,6,6-tetramethylpiperidine
Bis(1-heptyloxy-2,2,6,6-tetramethylpiperidin-4-yl) sebacate 1-Hexyloxy-4-methoxy-2,2,6,6-tetramethylpiperidine
Bis[1-(2-methyl-2-phenylpropyloxy)-2,2,6,6-tetramethylpiperidin-4-yl]adipate
1-(2-methyl-2-phenylpropyloxy)-4-benzoyloxy-2,2,6,6-tetramethylpiperidine
2-Chloro-4,6-bis[N-(1-cyclohexyloxy-2,2,6,6-tetramethylpiperidin-4-yl)butylamino]-s-triazine
2,4,6-Tris[N-(1-cyclohexyloxy-2,2,6,6-tetramethylpiperidin-4-yl)butylamino]-s-triazine
Bis(1-octyloxy-2,2,6,6-tetramethylpiperidin-4-yl) sebacate
1-Cyclooctyloxy-2,2,6,6-tetramethylpiperidin-4-ol
Reaction product of bis(1-oxyl-2,2,6,6-tetramethylpiperidin-4-yl) sebacate and methylcyclohexane
Reaction product of bis(1-oxyl-2,2,6,6-tetramethylpiperidin-4-yl) succinate and norbornane
Reaction product of 1-oxyl-2,2,6,6-tetramethylpiperidin-4-ol and decahydronaphthalene
Reaction product of bis(1-oxyl-2,2,6,6-tetramethylpiperidin-4-y) adipate and isooctane
Reaction product of 1-oxyl-4-benzoyloxy-2,2,6,6-tetramethylpiperidine and isooctane
Bis[1-(2,2-diphenylpropyloxy)-2,2,6,6-tetramethylpiperidin-4-yl]sebacate
1-Cyclohexyloxy-2,2,6,6-tetramethylpiperidine
Bis(1-octadecyloxy-2,2,6,6-tetramethylpiperidin-4-yl) succinate
1-Cyclohexyloxy-4-octadecanoyloxy-2,2,6,6-tetramethylpiperidine
1-Octyloxy-4-benzoyloxy-2,2,6,6-tetramethylpiperidine
1-Cyclohexyloxy-4-benzoyloxy-2,2,6,6-tetramethylpiperidine
1-Cyclohexyloxy-2,2,6,6-tetramethylpiperidin-4-ol
1-Cyclohexyloxy-2,2,6,6-tetramethylpiperidin-4-one The following examples are for illustrative purposes only and are not to be construed to limit the scope of the invention in any manner whatsoever.

EXAMPLE 1

1-Cyclohexyloxy-2,2,6,6-tetramethylpiperidin-4-ol

A solution of 80.2 g (1.18 mol) of 50% aqueous hydrogen peroxide is added at 70° C. over 12 hours to a mixture of 17.2 g (100 mmol) of 1-oxyl-2,2,6,6-tetramethylpiperidin-4-ol, 0.556 g (2.00 mmol) of iron(II) sulfate heptahydrate, 0.679 g (2.0 mmol) of tetrabutylammonium hydrogen sulfate, 0.15 ml (2.0 mmol) of methanesulfonic acid, 44 ml of cyclohexane, and 200 ml of methanol. Five hours after the peroxide addition is started, a solution of 0.556 g (2.0 mmol) of iron(II) sulfate heptahydrate and 0.15 ml (2.0 mmol) of methanesulfonic acid in 4 ml of water is added to the reaction mixture. Shortly after the peroxide addition is completed, the reaction mixture tests negative for hydrogen peroxide. Methanol is distilled from the reaction mixture at reduced pressure, and water and saturated sodium bicarbonate solution are added to the reaction mixture. A total of 60 ml of 12% by weight sodium borohydride in 14 N sodium hydroxide solution is added to the reaction mixture to convert any 4-oxo derivative of the title compound to the desired product. The reaction mixture is extracted with dichloromethane, and the organic layer is neutralized by the addition of hydrochloric acid followed by sodium bicarbonate. After drying, the organic layer is concentrated, and the crude product is purified by flash chromatography on silica gel to afford 15.0 g (59% yield) of the title compound, an off white solid having a melting point of 72-75° C. Structure is confirmed by mass spectrometry and NMR analysis.

EXAMPLE 2

1-Cyclohexyloxy-2,2,6,6-tetramethylpiperidin-4-one

A solution of 20.1 g (0.295 mol) of 50% aqueous hydrogen peroxide is added over 6 hours at 60° C. to a mixture of 8.51 g (50.0 mmol) of 1-oxyl-2,2,6,6-tetramethylpiperid-4-one, 0.70 g (2.5 mmol) of iron(II) sulfate heptahydrate, 0.3 ml (5 mmol) of methanesulfonic acid, 11 ml of cyclohexane, and 90 ml of methanol. Shortly after the addition is completed, the reaction mixture tests negative for hydrogen peroxide. The reaction mixture is concentrated to afford 4.4 g (35% yield) of the title compound, isolated as a yellow oil. Structure is confirmed by mass spectrometry and NMR analysis.

EXAMPLE 3

1-Cyclohexyloxy-2,2,6,6-tetramethylpiperidin-4-ol

A solution of 17.3 g (100 mmol) of 1-oxyl-2,2,6,6-tetramethylpiperidin-4-ol in 25 ml of water and a solution of 26.1 g (389 mmol) of 50% aqueous hydrogen peroxide are added dropwise over 1.25 hours and 6.5 hours, respectively, to a mixture of 0.578 g (2.1 mmol) of ferrous sulfate heptahydrate, 10 ml of water, 0.677 g (7.0 mmol) of methanesulfonic acid, 150 ml of acetonitrile, and 63 ml of cyclohexane at 60-62° C. Approximately 2 hours after the peroxide addition is started, a solution of 0.253 g (0.91 mmol) of ferrous sulfate heptahydrate and 0.331 g (3.4 mmol) of methanesulfonic acid in 1 ml of water is added to the reaction mixture. Approximately 4 hours after the peroxide addition is started, 15 ml of cyclohexane and a solution of 0.171 g (0.62 mmol) of ferrous sulfate heptahydrate and 0.242 g (2.5 mmol) of methanesulfonic acid in 1 ml of water are added to the reaction mixture. After the peroxide addition is completed, the reaction mixture is allowed to cool slowly to room temperature, and excess peroxide is destroyed by the addition of sodium sulfite. The crude reaction mixture is stirred with 2.4 g of solid sodium hydroxide, and the mixture is filtered. Isopropyl alcohol is added to the filtrate, and the filtrate is stirred at room temperature with 1.9 g of solid sodium borohydride to convert any 4-oxo derivative of the title compound to the title compound. The solution is diluted with acetonitrile (50 ml) and water (10 ml), and the organic layer is washed with 50% citric acid solution and saturated sodium bicarbonate solution. The organic layer is concentrated, and the concentrate is dissolved in a mixture of ethyl acetate, heptane, and water. The organic layer is passed through silica gel, and the silica gel is then eluted with a 1:1 mixture of heptane-ethyl acetate. Evaporation of the solvent affords 16.0 g (63% yield) of a white solid. Mass spectrometry and NMR analysis confirm that the reaction product is the title compound.

EXAMPLE 4

Bis(1-cyclohexyloxy-2,2,6,6-tetramethylpiperidin-4-yl) sebacate

A solution of 0.268 g (0.964 mmol) of ferrous sulfate heptahydrate and 0.350 g (3.64 mmol) of methanesulfonic acid in 3.7 g of water is added to a mixture of 10.3 g (20.2 mmol) of bis(1-oxyl-2,2,6,6-tetramethylpiperidin-4-yl) sebacate, 110 ml of acetonitrile, and 60 ml of cyclohexane. The mixture is heated to 55° C. A solution of 11.0 g (162 mmol) of 50% aqueous hydrogen peroxide is added dropwise to the reaction mixture over 4.75 hours while the reaction temperature is brought to and maintained at reflux. A solution of 0.098 g of ferrous sulfate heptahydrate and 0.128 g of methanesulfonic acid in 0.3 g of water is added to the reaction mixture 2.25 hours after the peroxide addition is started. A solution of 0.053 g of ferrous sulfate heptahydrate and 0.070 g of methanesulfonic acid in 0.4 g of water is added to the reaction mixture 4 hours after the peroxide addition is started. After all the peroxide is added, the reaction mixture is heated at reflux for 45 minutes. The reaction mixture is allowed to cool slowly to room temperature while stirring is continued. Peroxide is decomposed by the addition of 4.5 g of sodium sulfite. The aqueous layer is discarded, and after concentration of the organic solution, the crude product is purified by flash chromatography on silica gel with 20:1 heptane-ethyl acetate to afford 5.9 g (43% yield) of the title compound, a colorless oil. The structure of the reaction product is verified by NMR analysis.

EXAMPLE 5

1-Cyclohexyloxy-4-methoxy-2,2,6,6-tetramethylpiperidine

A solution of 0.246 g (0.885 mmol) of ferrous sulfate heptahydrate and 0.246 g (2.6 mmol) of methanesulfonic acid in 2 ml of water is added to a mixture of 4.85 g (26.0 mmol) of 1-oxyl-4-methoxy-2,2,6,6-tetramethylpiperidine, 35 ml of acetonitrile, and 22 ml of cyclohexane. The reaction mixture is heated to 52° C. A solution of 5.68 g (83 mmol) of 50% aqueous hydrogen peroxide is added dropwise to the reaction mixture over 2.5 hours while the reaction temperature is brought to and maintained at reflux (62° C). After the peroxide is added, the reaction mixture is stirred at reflux for 1.75 hours, and then allowed to cool slowly to 33° C. Peroxide is decomposed by the addition of aqueous sodium sulfite solution. The reaction mixture is diluted with ethyl acetate, and the organic layer is washed with water and then concentrated. Purification by flash chromatography with 20:1 heptane-ethyl acetate affords 4.11 g (59% yield) of the title compound, a colorless liquid. Structure is verified by NMR analysis.

EXAMPLE 6

Bis(1-heptyloxy-2,2,6,6-tetramethylpiperidin-4-yl) sebacate

A solution of 0.249 g (0.921 mmol) of ferric chloride hexahydrate and 0.327 g (3.3 mmol) of concentrated hydrochloric acid in 3.7 g of water is added to a mixture of 10.3 g (20.2 mmol) of bis(1-oxyl-2,2,6,6-tetramethylpiperidin-4-yl) sebacate, 110 ml of acetonitrile, and 80 ml of heptane. The reaction mixture is heated to 50° C. A solution of 10.9 g (160 mmol) of 50% aqueous hydrogen peroxide is added dropwise to the reaction mixture over 5.25 hours while the temperature is brought to and maintained at 65-68° C. A solution of 0.105 g of ferric chloride hexahydrate and 0.144 g of concentrated hydrochloric acid in 0.75 g of water is added to the reaction mixture 2.25 hours after the peroxide addition is started. A solution of 0.075 g of ferric chloride hexahydrate and 0.113 g of concentrated hydrochloric acid in 0.5 g of water is added to the reaction mixture 3.5 hours after the peroxide addition is started. After the peroxide is added, the reaction mixture is stirred at reflux for 15 minutes, then allowed to cool slowly for 1 hour to 33° C. Excess peroxide is decomposed with aqueous sodium sulfite solution. Work up and purification according to the procedure of Example 5 afford 5.81 g of a colorless oil. The NMR spectrum of the reaction product is consistent with a mixture of heptyl isomers of the title compound.

EXAMPLE 7

1-Hexyloxy-4-methoxy-2,2,6,6-tetramethylpiperidine

A solution of 0.268 g (0.964 mmol) of ferrous sulfate heptahydrate and 0.29 g (3.0 mmol) of methanesulfonic acid in 2 ml of water is added to a mixture of 4.81 g (25.8 mmol) of 1-oxyl-4-methoxy-2,2,6,6-tetramethylpiperidine, 25 ml of acetonitrile, and 21 ml of a mixture of hexanes. The reaction mixture is heated to 50° C. A solution of 7.0 g (103 mmol) of 50% aqueous hydrogen peroxide is added to the reaction mixture over 3.5 hours while the temperature is brought to and maintained at reflux (56°). After the peroxide is added, the reaction mixture is stirred at reflux for 1 hour, then allowed to cool slowly to room temperature. Work-up and purification following a procedure similar to that of Example 5 afford 1.80 g of a colorless oil. The NMR spectrum of the product is consistent with a mixture of hexyl isomers of the title compound. GC analysis shows the product comprises 3 materials with similar retention times in a ratio of 53:41:6 based on integration.

EXAMPLE 8

1-Octyloxy-4-benzoyloxy-2,2,6,6-tetramethylpiperidine

A solution of 0.234 g (0.87 mmol) of ferric chloride hexahydrate and 0.218 g (2.3 mmol) of concentrated hydrochloric acid in 2 ml of water is added to a mixture of 5.00 g (18.1 mmol) of 1-oxyl-4-benzoyloxy-2,2,6,6-tetramethylpiperidine, 25 ml of acetonitrile, and 16 ml of n-octane. The reaction mixture is heated to 55° C. A solution of 8.6 g (126 mmol) of 50% aqueous hydrogen peroxide is added dropwise to the reaction mixture over 4 hours while the temperature is brought to and maintained at 72-74° C. A solution of 0.104 g of ferric chloride hexahydrate and 0.140 g of concentrated hydrochloric acid in 0.5 ml of water is added to the reaction mixture 2.25 hours after the peroxide addition is started. After the peroxide is added, the reaction mixture is allowed to cool slowly to room temperature. Ethyl acetate and water are added to the reaction mixture, and the organic layer is concentrated and purified by flash chromatography with 25:1 heptane-ethyl acetate to obtain 3.69 g of a light yellow oil. GC analysis shows the reaction product contains 4 components with retention times that are consistent with the retention times of pure samples of the 4 possible octyl isomers of the title compound.

EXAMPLE 9

Bis[1-(2-methyl-2-phenylpropyloxy)-2,2,6,6-tetramethylpiperidin-4-yl] adipate

The title compound is prepared from the reaction of bis(1-oxyl-2,2,6,6-tetramethylpiperidin-4-yl) adipate, aqueous hydrogen peroxide, ferric chloride hexahydrate; acetonitrile, and tert-butylbenzene following a procedure similar to that of Example 6.

EXAMPLE 9A 1-(2-methyl-2-phenylpropyloxy)-4-benzoyloxy-2,2,6,6-tetramethylpiperidine A solution of 0.077 g (0.39 mmol) of ferrous chloride tetrahydrate in 2.2 g of water is added to a mixture of 5.00 g (18.1 mmol) of 1-oxyl-4-benzoyloxy-2,2,6,6-tetramethylpiperidine, 16 ml of t-butylbenzene, and 28 ml of acetonitrile that has been heated to 61° C. A solution of 5.03 g (74 mmol) of 50% aqueous hydrogen peroxide is added dropwise over 2 hours to the reaction mixture while the temperature is maintained at 65°. After the peroxide is added, the mixture is stirred for 1.25 hours at 65°. The reaction mixture is cooled to 30° and stirred with 20 ml of 10% aqueous sodium sulfite solution to decompose excess peroxide. The crude reaction mixture is diluted with ethyl acetate, and the organic layer is concentrated. Purification by flash chromatography with 100:1 and then 25:1 heptane-ethyl acetate affords 0.75 g (10% yield) of the title compound, a pale yellow oil. Structure is confirmed by NMR and mass spectrometry.

EXAMPLE 10

2-Chloro-4,6-bis[N-(1-cyclohexyloxy-2,2,6,6-tetramethylpiperidin-4-yl)butylamino]-s-triazine A solution of 0.188 g (0.676 mmol) of ferrous sulfate heptahydrate and 0.25 g (2.6 mmol) of methanesulfonic acid in 2 ml of water is added to a mixture of 5.00 g (8.83 mmol) of 2-chloro-4,6-bis[N-(1-oxyl-2,2,6,6-tetramethylpiperidin-4-yl)butylamino]-s-triazine, 29 ml of acetonitrile, and 18 ml of cyclohexane. The reaction mixture is heated to 52° C. A solution of 4.87 g (72 mmol) of 50% aqueous hydrogen peroxide is added dropwise to the reaction mixture over 2.25 hours while the temperature is brought to and maintained at 62° C. After the peroxide is added, the reaction mixture is stirred at reflux for 45 minutes, then cooled prior to decomposing residual peroxide with aqueous sodium sulfite. Work-up and purification according to the procedure of Example 5 afford 3.23 g (50% yield) of the title compound, a white glass. Structure is verified by NMR and ms analysis.

EXAMPLE 11

2,4,6-Tris[N-(1-cyclohexyloxy-2,2,6,6-tetramethylpiperidin-4-yl)butylamino]-s-triazine The title compound is prepared from the reaction of 2,4,6-tris[N-(1-oxyl-2,2,6,6-tetramethylpiperidin-4-yl)butylamino]-s-triazine and cyclohexane following a procedure similar to that of Example 10.

EXAMPLE 12

Bis(1-octyloxy-2,2,6,6-tetramethylpiperidin-4-yl) sebacate

A solution of 0.308 g (1.14 g) of ferric chloride hexahydrate and 0.225 g (3.75 mmol) of glacial acetic acid in 5 ml of water is added to a mixture of 10.00 g (19.6 mmol) of bis(1-oxyl-2,2,6,6-tetramethylpiperidin-4-yl) sebacate, 94 ml of acetonitrile, and 64 ml of n-octane that is heated to 76° C. The reaction mixture is kept at the reflux temperature of 76° as a solution of 11.52 g (169 mmol) of 50% aqueous hydrogen peroxide is added dropwise over 3 hours. A solution of 0.106 g of ferric chloride hexahydrate and 0.102 g of glacial acetic acid in 1.6 g of water is added to the reaction mixture 1.75 hours after the peroxide addition is begun. A solution of 0.106 g of ferric chloride hexahydrate and 0.073 g of glacial acetic acid in 1.6 g of water is added to the reaction mixture 2.75 hours after the peroxide addition is begun. The reaction mixture is maintained at the reflux temperature for 1 hour after the peroxide is added. Excess peroxide is decomposed by stirring the reaction mixture with aqueous sodium sulfite solution. Solids are removed by filtration. The aqueous layer of the filtrate is extracted with ethyl acetate. The combined organic layers are concentrated, and the concentrate is purified twice by flash chromatography with a 100:7.5 mixture of heptane-ethyl acetate to afford 4.43 g (31% yield) of the title compound, a colorless liquid. NMR analysis shows a mixture of octyl regioisomers.

EXAMPLE 13

1-Cyclohexyloxy-4-benzoyloxy-2,2,6,6-tetramethylipiperidine

A solution of 0.222 g (0.799 mmol) of ferrous sulfate heptahydrate and 0.287 g (3.0 mmol) of methanesulfonic acid in 3.7 g of water is added to a mixture of 10.3 g (37.3 mmol) of 1-oxyl-4-benzoyloxy-2,2,6,6-tetramethylpiperidine, 57 ml of acetonitrile, and 31 ml of cyclohexane. The reaction mixture is heated to 52° C. A solution of 10.2 g (150 mmol) of 50% aqueous hydrogen peroxide is added dropwise over 4.75 hours to the reaction mixture while the temperature is brought to and maintained at reflux (61° C.). A solution of 0.093 g of ferrous sulfate heptahydrate and 0.121 g of methanesulfonic acid in 0.4 g of water is added to the reaction mixture 1 hour after the peroxide addition is started. A solution of 0.066 g of ferrous sulfate heptahydrate and 0.090 g of methanesulfonic acid in 0.5 g of water is added to the reaction mixture 2.25 hours after the peroxide addition is started. After the peroxide is added, the reaction mixture is heated at reflux for 0.5 hour. Upon cooling, peroxide is decomposed by the addition of sodium sulfite. The organic layer is purified by flash chromatography on silica gel with 20:1 heptane-ethyl acetate to afford 8.77 g (65% yield) of the title compound, a white solid. GC assay is 99%.

A variety of transition metals are effective in the instant process, as summarized in Example 14.

EXAMPLE 14

1-Cyclohexyloxy-4-benzoyloxy-2,2,6,6-tetramethylipiperidine

A solution of metal salt, acid, and approximately 2 ml of water is added to a mixture of 5.00 g (18.1 mmol) of 1-oxyl-4-benzoyloxy-2,2,6,6-tetramethylpiperidine, 25-31 ml of acetonitrile, and 14-20 ml of cyclohexane. The reaction mixture is heated to 40-60° C. A solution of 4.3-5.5 9 of 50% aqueous hydrogen peroxide is added to the reaction mixture over 2-2.5 hours while the temperature is brought to and maintained at reflux (60-65° C.). After the peroxide is added, the reaction mixture is heated at reflux for 0-120 minutes, then allowed to cool slowly. Excess peroxide is decomposed by the addition of aqueous sodium sulfite solution. Work up and purification following a procedure similar to that of Example 5 afford the title compound. GC analysis is used to assay purity. Results appear in Table 1.

TABLE 1

Various Transition Metals Effective in the Instant Process

| Example | Equivalents of metal[a] | Equivalents of acid[a] | Isolated yield[b] |
|---|---|---|---|
| 14A | 0.039 Cu(CF$_3$SO$_3$)$_2$ | 0.13 CH$_3$SO$_3$H | 68% |
| 14B | 0.039 Cu(SO$_4$)$_2$ | 0.11 H$_2$SO$_4$ | 66% |
| 14C | 0.020 Co[(t-Bu$_2$salen)$_2$C$_6$H$_{10}$N$_2$]$_2$[c] | 0.086 CH$_3$SO$_3$H | 3% |

TABLE 1-continued

Various Transition Metals Effective in the Instant Process

| Example | Equivalents of metal[a] | Equivalents of acid[a] | Isolated yield[b] |
|---|---|---|---|
| 14D | 0.022 Mn[(t-Bu$_2$salen)$_2$C$_6$H$_{10}$N$_2$]$_2$Cl[d] | 0.080 CH$_3$SO$_3$H | 1.3% |
| 14E | 0.045 CoCl$_2$ | 0.15 CH$_3$SO$_3$H | 16% |
| 14F | 0.042 TiCl$_3$ | 0.45 HCl | 18% |
| 14G | 0.042 Ti(OC$_4$H$_9$)$_4$ | 0.30 HCl | 26% |
| 14H | 0.038 VCl$_3$ | 0.14 HCl | 14% |
| 14I | 0.039 MnCl$_2$ | 0.14 HCl | 26% |
| 14J | 0.039 VCl$_2$ | 0.13 HCl | 17% |
| 14K | 0.039 (C$_4$H$_9$)$_2$SnO | 0.13 HCl | 7% |
| 14L | 0.041 CuCl$_2$ | 0.14 HCl | 48% |
| 14M | 0.037 SnCl$_4$ | 0.14 HCl | 1% |
| 14N | 0.039 Ti(OCH$_3$)$_4$ | 0.15 HCl | 1% |
| 14O | 0.041 CeCl$_3$ | 0.13 HCl | 45% |

[a]per mole of 1-oxyl hindered amine
[b]yield of 1-cyclohexyloxy-4-benzoyloxy-2,2,6,6-tetramethyliperidine, based on 1-oxyl starting material
[c]Co[(t-Bu$_2$salen)$_2$C$_6$H$_{10}$N$_2$]$_2$ is (R,R)-(−) N,N'-bis(3,5-di-tert-butylsalicylidene)-1,2-cyclohexanediaminocobalt(II)
[d]Mn[(t-Bu$_2$salen)$_2$C$_6$H$_{10}$N$_2$]$_2$Cl is (R,R)-(−) N,N'-bis(3,5-di-tert-butylsalicylidene)-1,2-cyclohexanediaminomanganese(III) chloride Examples 15A-B shows that a hydrogen peroxide equivalent can be used in place of hydrogen peroxide in the instant process.

EXAMPLE 15A

1-Cyclohexyloxy-4-benzoyloxy-2,2,6,6-tetramethyliperidine

A solution of 0.191 g (0.566 mmol) of iron(II) tetrafluoroborate hexahydrate and 0.261 g (1.43 mmol) of 48% tetrafluoroboric acid in 2 ml of water is added to a mixture of 5.00 g (18.1 mmol) of 1-oxyl-4-benzoyloxy-2,2,6,6-tetramethylpiperidine, 26 ml of acetonitrile, and 17 ml of cyclohexane. The reaction mixture is heated to 46° C. A solution of 5.15 g (76 mmol) of 50% aqueous hydrogen peroxide is added to the reaction mixture over 2.25 hours while the temperature is brought to and maintained at reflux (62° C.). A solution of 0.067 g of iron(II) tetrafluoroborate hexahydrate and 0.139 g of 48% tetrafluoroboric acid in 0.5 ml of water is added to the reaction mixture 1 hour after the peroxide addition is started. After the peroxide is added, the reaction mixture is heated at reflux for 45 minutes, then allowed to cool slowly. Excess peroxide is decomposed by the addition of aqueous sodium sulfite solution. Work up and purification following a procedure similar to that of Example 5 afford 4.98 g (77% yield) of the title compound, a colorless syrup.

EXAMPLE 15B

1-Cyclohexyloxy-4-benzoyloxy-2,2,6,6-tetramethyliperidine

The procedure of Example 15A is repeated with a solution of 5.89 g (63 mmol) of urea hydrogen peroxide addition compound dissolved in 11 g of water used in place of 50% aqueous hydrogen peroxide. The peroxide solution is added to the reaction mixture over 3-3.25 hours. The yield of the title compound is 3.97 g (61% yield).

EXAMPLE 16

1-Cyclooctyloxy-2,2,6,6-tetramethylpiperidin-4-ol

The title compound is prepared from 1-oxyl-2,2,6,6-tetramethylpiperidin-4-ol and cyclooctane following a procedure to that of Example 5.

EXAMPLE 17

Reaction product of bis(1-oxyl-2,2,6,6-tetramethylpiperidin-4-yl) sebacate and methylcyclohexane Bis(1-oxyl-2,2,6,6-tetramethylpiperidin-4-yl) sebacate and methylcyclohexane are reacted following a procedure similar to that of Example 6. The reaction product comprises a mixture of regioisomers.

EXAMPLE 18

Reaction Product of bis(1-oxyl-2,2,6,6-tetramethylpiperidin-4-yl) succinate and norbornane Bis(1-oxyl-2,2,6,6-tetramethylpiperidin-4-y) succinate and norbornane are reacted following a procedure similar to that of Example 6.

EXAMPLE 19

Reaction Product of 1-oxyl-2,2,6,6-tetramethylpiperidin-4-ol and decahydronaphthalene 1-Oxyl-2,2,6,6-tetramethylpiperidin-4-ol and decahydronaphthalene (decalin) are reacted following a procedure similar to Example 5.

EXAMPLE 20

Reaction Product of bis(1-oxyl-2,2,6,6-tetramethylpiperidin-4-y) adipate and isooctane Bis(1-oxyl-2,2,6,6-tetramethylpiperidin-4-yl) adipate and isooctane (2,2,4-trimethylpentane) are reacted following a procedure similar to that of Example 6.

EXAMPLE 20A

Reaction Product of 1-oxyl-4-benzoyloxy-2,2,6,6-tetramethylpiperidine and isooctane A solution of 0.101 g (0.374 mmol) of ferric chloride hexahydrate and 0.160 g (2.66 mmol) of glacial acetic acid in 2 ml of water is added to a mixture of 5.00 g (18.1 mmol) of 1-oxyl-4-benzoyloxy-2,2,6,6-tetramethylpiperidine, 27 ml of 2,2,4-trimethylpentane (isooctane), and 40 ml of acetonitrile that has been heated to reflux. A solution of 5.25 g (77 mmol) of 50% aqueous hydrogen peroxide is added to the reaction mixture dropwise over 3.25 hours while the reaction temperature is maintained at 65°. A solution of 0.050 g of ferric chloride hexahydrate and 0.053 g of acetic acid in 1 ml of water is added to the reaction mixture 1 hour after the peroxide addition is begun. The reaction mixture is heated at 65° for 2.5 hours after the peroxide is added, then cooled. The mixture is stirred with 5 ml of 10% aqueous sodium sulfite solution and the organic layer is concentrated. Purification by flash chromatography with 20:1 heptane-ethyl acetate affords 2.27 g of a colorless liquid. Analysis by gas chromatography reveals 4 components in the ratio of 0.38:0.53:0.02:0.07. The NMR spectrum of the product is consistent with a mixture of isooctyl regioisomers.

EXAMPLE 21

Bis[1-(2,2-diphenylpropyloxy)-2,2,6,6-tetramethylpiperidin-4-yl] sebacate

Bis(1-oxyl-2,2,6,6-tetramethylpiperidin-4-y) sebacate and 2,2-diphenylpropane are reacted following a procedure similar to that of Example 6.

EXAMPLE 22

1-Cyclohexyloxy-2,2,6,6-tetramethylpiperidine

The title compound is prepared from the reaction of 1-oxyl-2,2,6,6-tetramethylpiperidine (TEMPO) and cyclohexane according to the procedure of Example 5.

EXAMPLE 23

Bis(1-octadecyloxy-2,2,6,6-tetramethylpiperidin-4-yl) succinate

The title compound is prepared from the reaction of bis(1-oxyl-2,2,6,6-tetramethylpiperidin-4-yl) succinate and octadecane following a procedure similar to that of Example 4.

EXAMPLE 24

1-Cyclohexyloxy-4-octadecanoyloxy-2,2,6,6-tetramethylpiperidine

A solution of 0.116 g (0.429 mmol) of ferric chloride hexahydrate and 0.096 g (1.60 mmol) of glacial acetic acid in 2 ml of water is added to a mixture of 5.08 g (11.6 mmol) of 1-oxyl-4-octadecanoyloxy-2,2,6,6-tetramethylpiperidine, 40 ml of cyclohexane, and 60 ml of acetonitrile that has been heated to 60°. A solution of 3.36 g (49.4 mmol) of aqueous 50% hydrogen peroxide is added to the reaction mixture dropwise over 2.5 hours at the reflux temperature of 60-62°. A solution of 0.033 g of ferric chloride hexahydrate and 0.040 g of glacial acetic acid in 1 ml of water is added to the reaction mixture 1.5 hours after the peroxide addition is begun. A solution of 0.031 g of ferric chloride and 0.028 g of glacial acetic acid in 1 ml of water is added to the reaction mixture 4 hours after the peroxide addition is begun. After being heated a total of 5 hours at reflux temperature, the reaction mixture is cooled and excess peroxide is decomposed by the addition of aqueous sodium sulfite solution. The organic layer is concentrated and purified by flash chromatography with 20:1 heptane-ethyl acetate to afford 4.27 g (71% yield) of the title compound, a white solid, mp 42-46. The assay is approximately 90% by NMR integration.

Examples 25 and 26 demonstrate that the instant process can be carried out below the reflux temperature of the reaction mixture.

EXAMPLE 25

1-Cyclohexyloxy-4-benzoyloxy-2,2,6,6-tetramethylpiperidine

The procedure of Example 13 is repeated, except that the amount of each of the reactants is reduced by a factor of approximately 2, and the reaction temperature is maintained at 38-43° C. The yield of the title compound, a colorless syrup, is 2.82 g, which corresponds to a 43% yield.

EXAMPLE 26

1-Cyclohexyloxy-4-benzoyloxy-2,2,6,6-tetramethylpiperidine

The procedure of Example 15A is repeated, except that the reaction temperature is maintained at 20-22° C. The yield of the title compound, a colorless syrup, is 1.99 g, which corresponds to a 31% yield.

Examples 27A-D show that the amount of metal salt catalyst in the instant process can be reduced to less than 0.005 equivalents before yield drops significantly.

EXAMPLE 27A

1-Cyclohexyloxy-4-benzoyloxy-2,2,6,6-tetramethylpiperidine

A solution of 0.100 g (0.36 mmol, 0.020 equivalents) of ferrous sulfate heptahydrate and 0.314 g (1.7 mmol) of 48% tetrafluoroboric acid in 2 ml of water is added to a mixture of 5.00 g (18.1 mmol) of 1-oxyl-4-benzoyloxy-2,2,6,6-tetramethylpiperidine, 26 ml of acetonitrile, and 18 ml of cyclohexane. The mixture is heated to 46° C. A solution of 4.9 g (72 mmol) of 50% aqueous hydrogen peroxide is added dropwise over 2.25 hours to the reaction mixture while the temperature is brought to and maintained at reflux. After the peroxide is added, the reaction mixture is heated at reflux for 1 hour, then allowed to cool slowly to room temperature. Residual peroxide is decomposed with aqueous sodium sulfite solution. Ethyl acetate is added to the reaction mixture, and the organic layer is concentrated. Purification by flash chromatography on silica gel with 20:1 heptane-ethyl acetate afford 5.06 g (78% yield) of a white solid. GC analysis shows the reaction product, which has an assay of 100%, has the same retention time as an authentic sample of the title compound.

EXAMPLE 27B

1-Cyclohexyloxy-4-benzoyloxy-2,2,6,6-tetramethylpiperidine

The procedure of Example 27A is repeated, except that the amount of ferrous sulfate heptahydrate is reduced to 0.051 g (0.18 mmol) or 0.010 equivalents, to afford 4.66 g (71% yield) of the title compound.

EXAMPLE 27C

1-Cyclohexyloxy-4-benzoyloxy-2,2,6,6-tetramethylpiperidine

The procedure of Example 27A is repeated, except that the amount of ferrous sulfate heptahydrate is reduced to 0.026 g (0.094 mmol) or 0.0052 equivalents, to afford 4.78 g (74% yield) of the title compound.

EXAMPLE 27D

1-Cyclohexyloxy-4-benzoyloxy-2,2,6,6-tetramethylpiperidine

The procedure of Example 27A is repeated, except that the amount of ferrous sulfate heptahydrate used is 0.0050 g ($\frac{1}{20}^{th}$ of a solution of 0.100 g of ferrous sulfate heptahydrate diluted with water to a mass of 20.01 g) or 0.0179 mmol (0.00099 equivalents). The yield of the title compound after work-up and purification by flash chromatography is 1.06 g (16% yield).

Examples 28 and 29 show that acetonitrile gives superior results to methanol when used as the cosolvent in the instant process.

EXAMPLE 28

1-Cyclohexyloxy-4-benzoyloxy-2,2,6,6-tetramethylpiperidine

A solution of 0.101 g (0.37 mmol) of ferric chloride hexahydrate and 0.115 g (1.9 mmol) of glacial acetic acid in 2 ml of water is added to a mixture of 5.00 g (18.1 mmol) of 1-oxyl-4-benzoyloxy-2,2,6,6-tetramethylpiperidine, 27 ml of methanol, and 18 ml of cyclohexane. The mixture is heated to reflux, 55° C. A solution of 4.9 g (72 mmol) of 50% aqueous hydrogen peroxide is added dropwise over 2.25 hours to the reaction mixture while the temperature is brought to and maintained at reflux. After the peroxide is added, the reaction mixture tests negative for hydrogen peroxide. The yield of the title compound, after work-up with ethyl acetate and purification by flash chromatography, is 2.63 g (40% yield, GC assay 100%).

EXAMPLE 29

1-Cyclohexyloxy-4-benzoyloxy-2,2,6,6-tetramethylpiperidine

The procedure of Example 28 is repeated, except that acetonitrile (27 ml) is used in place of methanol. The peroxide addition time is 3.25 hours, and the reflux temperature is 62° C. After the peroxide is added, the reaction mixture is heated at reflux for 90 minutes. Work-up and purification according to the procedure of Example 5 afford 5.38 g (83% yield) of the title compound, a colorless syrup. GC assay: 99.4%.

Examples 30 and 30A demonstrate that excellent yields of N-hydrocarbyloxy hindered amine derivatives can be obtained with boric acid and citric acid.

EXAMPLE 30

1-Cyclohexyloxy-4-benzoyloxy-2,2,6,6-tetramethylpiperidine

A solution of 0.100 g (0.360 mmol) of ferrous sulfate heptahydrate and 0.112 g (1.82 mmol) of boric acid in 4 ml of water is added to a mixture of 5.00 g (18.1 mmol) of 1-oxyl-4-benzoyloxy-2,2,6,6-tetramethylpiperidine, 27 ml of acetonitrile, and 19 ml of cyclohexane. The mixture is heated to 52° C. A solution of 4.98 g (73 mmol) of 50% aqueous hydrogen peroxide is added dropwise over 2.75 hours to the reaction mixture while the temperature is brought to and maintained at reflux (63° C.). A solution of 0.051 g of ferrous sulfate heptahydrate and 0.042 g of boric acid in 2 ml of water is added to the reaction mixture 1.25 hours after the peroxide addition is started. After the peroxide is added, the reaction mixture is heated at reflux for 30 minutes, then allowed to cool slowly. Work-up and purification according to the procedure of Example 5 afford 4.42 g (68% yield) of the title compound, a colorless syrup, GC assay 99.3%.

EXAMPLE 30A

1-Cyclohexyloxy-2,2,6,6-tetramethylpiperidin-4-one

A solution of 0.104 g (0.523 mmol) of ferrous chloride tetrahydrate and 0.168 g (0.799 mmol) of citric acid monohydrate in 1.5 ml of water is added to a mixture of 3.14 g (18.4 mmol) of 1-oxyl-2,2,6,6-tetramethylpiperidin-4-one, 30 ml of acetonitrile, and 20 ml of cyclohexane that has been heated to the reflux temperature of 60°. A solution of 5.27 g (77 mmol) of 50% aqueous hydrogen peroxide is added dropwise over 2 hours to the reaction mixture while the temperature is maintained at reflux. A solution of 0.047 g of ferrous chloride tetrahydrate and 0.055 g of citric acid monohydrate in 0.5 ml of water is added to the reaction mixture 1.6 hours after the peroxide addition is started. After the peroxide is added, the reaction mixture is heated at reflux for 30 minutes, then allowed to cool slowly. Aqueous sodium sulfite solution is added to the reaction mixture to decompose excess peroxide. The aqueous layer is extracted with a 2:1 mixture of acetonitrile-cyclohexane and then with ethyl acetate. The combined organic layers are concentrated. Purification by flash chromatography with 20:1 heptane-ethyl acetate affords 3.01 g (64% yield) of the title compound as a colorless liquid. GC assay is 99%.

Examples 31-33 show that in some cases, the instant procedure gives excellent yields without adding acid.

EXAMPLE 31

1-Cyclohexyloxy-4-benzoyloxy-2,2,6,6-tetramethylpiperidine

A solution of 0.097 g (0.359 mmol) of ferric chloride hexahydrate in 2 ml of water is added to a mixture of 5.00 g (18.1 mmol) of 1-oxyl-4-benzoyloxy-2,2,6,6-tetramethylpiperidine, 28 ml of acetonitrile, and 19 ml of cyclohexane. The mixture is heated to 56° C. A solution of 4.70 g (69 mmol) of 50% aqueous hydrogen peroxide is added dropwise over 2.25 hours to the reaction mixture while the temperature is brought to and maintained at reflux. After the peroxide is added, the mixture is heated at reflux for 45 minutes. Work-up and purification according to the procedure of Example 5 afford 5.47 g (84% yield) of the title compound, a pale yellow syrup. GC assay is 100%.

EXAMPLE 32

1-Cyclohexyloxy-4-benzoyloxy-2,2,6,6-tetramethylpiperidine

The procedure of Example 31 is repeated, except that ferrous chloride tetrahydrate (0.071 g, 0.357 mmol) is used in place of ferric chloride hexahydrate. The yield of the title compound is 4.69 g (72% yield, GC assay 100%).

EXAMPLE 33

1-Cyclohexyloxy-4-benzoyloxy-2,2,6,6-tetramethylpiperidine

The procedure of Example 31 is repeated, except that 0.072 g (0.42 mmol) of cupric chloride is used in place of ferric chloride hexahydrate. The yield of the title compound is 4.40 g (68% yield, GC assay 98%).

Example 34 shows that in certain instances, omitting acid from the reaction can significantly reduce the yield of N-hydrocarbyloxy product.

EXAMPLE 34

1-Cyclohexyloxy-4-benzoyloxy-2,2,6,6-tetramethylpiperidine

A solution of 0.121 g (0.358 mmol) of iron(II) tetrafluoroborate hexahydrate in 2 ml of water is added to a mixture of 5.00 g (18.1 mmol) of 1-oxyl-4-benzoyolxy-2,2,6,6-tetramethylpiperidine, 27 ml of acetonitrile, and 18 ml of cyclohexane. The mixture is heated to 49° C. A solution of 4.76 g (70.0 mmol) of 50% aqueous hydrogen peroxide is added dropwise over 2.25 hours to the reaction mixture while the temperature is brought to and maintained at reflux. After the peroxide is added, the mixture is heated at reflux for 45 minutes. Work-up and purification according to the procedure of Example 5 afford 0.37 g (6% yield) of the title compound, a pale yellow syrup. GC assay is 99.3%.

The 6% yield obtained by the procedure of Example 34 is compared to the 77% yield obtained by the procedure of Example 15A. The two procedures are essentially identical, except that in Example 15A, tetrafluoroboric acid is added to the reaction mixture.

The effect of changing the ratio of cosolvent to hydrocarbon solvent is illustrated in Examples 35-39.

EXAMPLE 35

1-Cyclohexyloxy-4-benzoyloxy-2,2,6,6-tetramethylpiperidine

The procedure of Example 31 is repeated using 169 ml of acetonitrile and 17 ml of cyclohexane to afford 4.64 g (71% yield) of the title compound, GC assay 100%.

EXAMPLE 36

1-Cyclohexyloxy-4-benzoyloxy-2,2,6,6-tetramethylpiperidine

The procedure of Example 31 is repeated using 85 ml of acetonitrile and 17 ml of cyclohexane to afford 5.19 g (80% yield) of the title compound, GC assay 100%.

EXAMPLE 37

1-Cyclohexyloxy-4-benzoyloxy-2,2,6,6-tetramethylpiperidine

The procedure of Example 31 is repeated using 10 ml of acetonitrile and 20 ml of cyclohexane to afford 3.82 g (59% yield) of the title compound, GC assay 98%.

EXAMPLE 38

1-Cyclohexyloxy-4-benzoyloxy-2,2,6,6-tetramethylpiperidine

The procedure of Example 31 is repeated using 4 ml of acetonitrile and 20 ml of cyclohexane to afford 0.72 g (11% yield) of the title compound, GC assay 96%.

EXAMPLE 39

1-Cyclohexyloxy-4-benzoyloxy-2,2,6,6-tetramethylpiperidine

The procedure of Example 31 is repeated using 2 ml of acetonitrile and 20 ml of cyclohexane to afford 0.11 g (2% yield) of the title compound, GC assay 92%.

The procedures of Example 40A-C, adapted from the methodology of Barton, et al., in *Tetrahedron*, 1996, 52, 10301-12, are compared to the procedures of Examples 13 and 31 to show the advantages of the instant process over prior art.

EXAMPLE 40A

1-Cyclohexyloxy-4-benzoyloxy-2,2,6,6-tetramethylpiperidine

To a mixture of 3.01 g (10.9 mmol) of 1-oxyl-4-benzoyloxy-2,2,6,6-tetramethylpiperidine, 20 ml of pyridine, and 12 ml of cyclohexane are added 0.153 g (0.55 mmol) of ferrous sulfate heptahydrate, 0.211 g (1.71 mmol) of picolinic acid, and 0.048 g (0.27 mmol) of ascorbic acid. Water (1 ml) is added to dissolve the metal salt. The mixture is heated to 48° C. A solution of 2.95 g (43.5 mmol) of 50% aqueous hydrogen peroxide is added dropwise over 1.25 hours to the reaction mixture while the temperature is brought to and maintained at 60-64° C. After the peroxide is added, the reaction mixture is allowed to cool slowly. After the reaction mixture is stirred overnight at room temperature, residual peroxide is decomposed by the addition of aqueous sodium sulfite solution. A mixture of 15 ml of concentrated sulfuric acid and 65 g of ice is carefully added to the reaction mixture to form a salt from the pyridine. The reaction mixture is extracted twice with ethyl acetate. The combined organic layers are washed with dilute sodium bicarbonate solution and saturated sodium chloride solution, then concentrated. Purification by flash chromatography on silica gel with 20:1 heptane-ethyl acetate affords 2.03 g (52% yield) of the title compound, a colorless syrup, GC assay 100%.

EXAMPLE 40B

1-Cyclohexyloxy-4-benzoyloxy-2,2,6,6-tetramethylpiperidine

To a mixture of 3.00 g (10.9 mmol) of 1-oxyl-4-benzoyloxy-2,2,6,6-tetramethylpiperidine, 20 ml of pyridine, and 12 ml of cyclohexane are added 2.2 ml (38.4 mmol, 3.5 equivalents) of glacial acetic acid, 1 ml of water, 0.124 g (0.446 mmol) of ferrous sulfate heptahydrate, and finally, 0.57 g (8.7 mmol, 0.80 equivalents) of zinc powder. A slight exothermic reaction occurs upon the addition of zinc. The reaction mixture is heated to 45° C. A solution of 3.0 g (44 mmol) of 50% aqueous hydrogen peroxide is added dropwise over 1.5 hours to the reaction mixture while the temperature is brought to and maintained at 60-64° C. After the peroxide is added, the mixture is heated at 62° C. for 15 minutes, then allowed to cool slowly. After the reaction mixture is stirred overnight at room temperature, residual peroxide is decomposed by the addition of aqueous sodium sulfite solution. A mixture of 15 ml of concentrated sulfuric acid and 76 g of ice is carefully added to the reaction mixture to form a salt from the pyridine. Work-up and purification according to the procedure of Example 40A afford 2.07 g (53% yield) of the title compound, a white solid, GC assay 100%.

EXAMPLE 40C

1-Cyclohexyloxy-4-benzoyloxy-2,2,6,6-tetramethylpiperidine

A solution of 0.202 g (0.73 mmol) of ferrous sulfate heptahydrate and 0.214 g (2.23 mmol) of methanesulfonic acid in 2.2 g of water are added to a mixture of 5.00 g (18.1 mmol) of 1-oxyl-4-benzoyloxy-2,2,6,6-tetramethylpiperidine, 33 ml of pyridine, and 21 ml of cyclohexane. The reaction mixture is heated to 46° C. A solution of 4.86 g (71 mmol) of 50% hydrogen peroxide is added dropwise over 2.25 hours to the reaction mixture while the temperature is brought to and maintained at 60-65° C. After the peroxide is added, the reaction mixture is allowed to cool slowly. The mixture is stirred overnight at room temperature. Residual peroxide is decomposed by the addition of aqueous sodium sulfite.

A mixture of 25 ml of concentrated sulfuric acid and 125 g of ice is carefully added to the reaction mixture to form a salt from the pyridine. Work-up and purification according to the procedure of Example 40A afford 1.93 g (30% yield) of the title compound, a white solid, GC assay 100%.

The 30-53% yields obtained in Examples 40A-C are compared to the 65% and 84% yields obtained in Examples 13 and 31, respectively, without the use of pyridine solvent, ascorbic acid, or zinc metal. This comparison shows that the instant process is less complicated and gives higher yields of N-hydrocarbyloxy product than the prior art methods of Barton, et al.

Examples 41-44 illustrate that the instant process can be modified to synthesize N-hydrocarbyloxy compounds starting from hindered amines without isolation of the N-oxyl intermediate.

EXAMPLE 41

1-Cyclohexyloxy-2,2,6,6-tetramethylpiperidin-4-ol

A mixture of 5.21 g (33.1 mmol) of 2,2,6,6-tetramethylpiperidin-4-ol, 0.015 g (0.142 mmol) of anhydrous sodium carbonate, 15 ml of water, and 15 ml of acetonitrile is heated to 56° C. A solution of 6.5 g (96 mmol) of 50% aqueous hydrogen peroxide is added to the reaction mixture over 1.5 hours while the temperature is brought to and maintained at 80° C. After the peroxide is added, the reaction mixture is heated at 80° C. for 3 hours, then cooled slowly to 50° C. over 1.75 hours. The mixture is kept at ambient temperature overnight. A solution of 0.184 g (0.662 mmol) of ferrous sulfate heptahydrate and 0.664 g (3.6 mmol) of 48% tetrafluoroboric acid in 2 ml of water is added to the reaction mixture, followed by 30 ml of cyclohexane and 24 ml of acetonitrile. The reaction mixture is heated to 50° C. A solution of 8.7 g (128 mmol) of 50% aqueous peroxide is added to the reaction mixture dropwise over 4.5 hours while the temperature is brought to and maintained at 62° C. After the peroxide is added, the reaction mixture is stirred at reflux for 1 hour. Upon cooling, residual peroxide is decomposed by the addition of aqueous sodium sulfite solution. Work-up with ethyl acetate and purification by flash chromatography afford 2.03 g (24% overall yield) of a white solid. GC analysis shows that the reaction product has a retention time identical to that of an authentic sample of the title compound.

In Example 41A, an excellent yield is obtained when less water is used in the oxidation reaction and the aqueous layer is removed prior to conversion of the N-oxyl intermediate to the final product.

EXAMPLE 41 A

1-Cyclohexyloxy-2,2,6,6-tetramethylpiperidin-4-ol

A mixture of 0.107 g (1.27 mmol) of sodium bicarbonate in 3 ml of water is added to a mixture of 10.00 g (63.6 mmol) of 2,2,6,6-tetramethylpiperidin-4-ol and 8 ml of acetonitrile that has been heated to 60° C. A solution of 9.80 g (144 mmol) of 50% aqueous hydrogen peroxide is added to the reaction mixture dropwise over 2.5 hours as the reaction temperature is maintained at 70-72° C. Upon cooling the reaction mixture is diluted with acetonitrile and cyclohexane, and then saturated sodium chloride solution and solid sodium chloride are added. The aqueous layer is extracted three times with a mixture of cyclohexane and acetonitrile. The aqueous layer is discarded. To the combined organic layers are added cyclohexane and acetonitrile to bring the total amount of solvent to 70 ml and 105 ml, respectively. The reaction mixture is heated to near reflux, and a solution of 0.532 g (1.97 mmol) of ferric chloride hexahydrate and 0.602 g (6.26 mmol) of methanesulfonic acid in 5 ml of water is added over several minutes. A solution of 16.50 g (243 mmol) of 50% aqueous hydrogen peroxide is added to the reaction mixture dropwise over 4.25 hours as the reaction temperature is maintained at reflux (61° C.). A solution of 0.163 g of ferric chloride hexahydrate and 0.198 g of methanesulfonic acid in 2 ml of water is added to the reaction mixture 2.25 hours after the peroxide addition is begun. A solution of 0.083 g of ferric chloride hexahydrate and 0.117 g of methanesulfonic acid in 1 ml of water is added to the reaction mixture 3.25 hours after the peroxide addition is begun. The reaction mixture is heated at 50-60° C. for 30 minutes after the peroxide is added. Work up according to the procedure of Example 54 gives 11.95 g (74% yield) of the title compound, GC assay 87%.

EXAMPLE 41B

1-Cyclohexyloxy-2,2,6,6-tetramethylpiperidin-4-ol

The procedure of Example 41A is repeated with an equivalent amount of ammonium carbonate used in place of sodium bicarbonate to obtain a 54% yield of the title compound. GC assay is 92%.

Examples 41C and D show that the oxidation reaction can be carried out a lower temperature by adding sodium tungstate to the reaction mixture.

EXAMPLE 41C

1-Cyclohexyloxy-2,2,6,6-tetramethylpiperidin-4-ol

A mixture of 0.108 g (1.29 mmol) of sodium bicarbonate and 0.265 g (0.803 mmol) of sodium tungstate dihydrate in 2 ml of water is added to a mixture of 10.00 g (63.6 mmol) of 2,2,6,6-tetramethylpiperidin-4-ol and 9 ml of acetonitrile. A solution of 12.11 g (178 mmol) of 50% aqueous hydrogen peroxide is added to the reaction mixture dropwise over 3.75 hours as the reaction temperature is maintained at 35-38° C. The reaction mixture is heated at 35-38° C. for an additional 2 hours. The reaction mixture is diluted with acetonitrile and cyclohexane, and then saturated sodium chloride solution and solid sodium chloride are added. The aqueous layer is extracted twice with a mixture of cyclohexane and acetonitrile. The aqueous layer is discarded. To the combined organic layers are added cyclohexane and acetonitrile to bring the total amount of solvent to 65 ml and 95 ml, respectively. The reaction mixture is heated to near reflux, and a solution of 0.528 g (1.95 mmol) of ferric chloride hexahydrate and 0.628 g (6.53 mmol) of methanesulfonic acid in 5 ml of water is added over several minutes. A solution of 17.22 g (253 mmol) of 50% aqueous hydrogen peroxide is added to the reaction mixture dropwise over 4.75 hours as the reaction temperature is maintained at reflux (60° C.). A solution of 0.170 g of ferric chloride hexahydrate and 0.206 g of methanesulfonic acid in 2 ml of water is added to the reaction mixture 2.5 hours after the peroxide addition is begun. A solution of 0.178 g of ferric chloride hexahydrate and 0.205 g of methanesulfonic acid in 2 ml of water is added to the reaction mixture 4 hours after the peroxide addition is begun. The reaction mixture is heated at reflux for 30 minutes after the peroxide is added. Work up according to the procedure of Example 54 gives 11.07 g (68% yield) of the title compound. GC assay is 92%.

Example 41D demonstrates that when the water layer from step 1 is not removed from the reaction mixture prior to the beginning of step 2, the second step is less efficient in terms of yield and quantities of reagents used.

EXAMPLE 41D

1-Cyclohexyloxy-2,2,6,6-tetramethylpiperidin-4-ol

The procedure of Example 41C is repeated, except that the reaction mixture containing the N-oxyl intermediate is used as is, without extracting and discarding the aqueous layer, prior to the introduction of the aqueous solution of ferric chloride hexahydrate and methanesulfonic acid. Approximately 40% more ferric chloride hexahydrate, methanesulfonic acid, and 50% aqueous hydrogen peroxide are used compared to Example 41C, and GC analysis shows that the reaction proceeds to only 90% conversion to the title compound. The yield of the title compound is 9.75 g (60% yield). GC assay is 91%.

EXAMPLE 42

1-Cyclohexyloxy-4-octadecanoyloxy-2,2,6,6-tetramethylpiperidine

A solution of 2.84 g (41.7 mmol) of 50% aqueous hydrogen peroxide is added dropwise over 3 hours to a mixture of 5.98 g (14.1 mmol) of 4-octadecanoyloxy-2,2,6,6-tetramethylpiperidine, 0.026 g (0.31 mmol, 2.2 mole percent) of sodium bicarbonate dissolved in 0.6 g of water, 4 ml of cyclohexane, and 4 ml of acetonitrile while the reaction temperature is maintained at 65-68° C. After the peroxide is added, the reaction mixture is stirred at 65° C. for 4.5 hours. The red mixture is cooled, and then diluted with cyclohexane and acetonitrile. The aqueous layer is discarded. The mixture is washed with water, and the wash is extracted with a mixture of cyclohexane and acetonitrile. A total of 25 ml each of cyclohexane and acetonitrile are used in the work up. The organic layers are combined, and more acetonitrile (13 ml) is added. The temperature is brought to 50° C., and a solution of 0.117 g (0.433 mmol) of ferric chloride hexahydrate and 0.096 g (1.60 mmol) of glacial acetic acid in 2 ml of water is added to the reaction mixture. A solution of 4.28 g (63 mmol) of 50% aqueous peroxide is added dropwise over 3 hours to the reaction mixture while the temperature is maintained near 60° C. A solution of 0.042 g of ferric chloride hexahydrate, 0.5 g of water, and 0.044 g of glacial acetic acid is added to the reaction mixture 1.5 hours after the peroxide addition is begun. The mixture is heated at reflux for 4 hours after the peroxide is added, then allowed to stand at room temperature overnight. Glacial acetic acid (0.403 g, 6.7 mmol) and a solution of 0.130 g of ferric chloride hexahydrate in 0.5 g of water are added to the red reaction mixture. The temperature is brought to reflux, and a solution of 4.56 g (67.0 mmol) of 50% aqueous hydrogen peroxide is added dropwise over 2 hours. A solution of 0.070 g of ferric chloride hexahydrate and 0.096 g of glacial acetic acid in 1 ml of water is added to the reaction mixture 1 hour after the peroxide addition is begun. The mixture is heated at reflux for 2.5 hours after the peroxide is added. The mixture is cooled and stirred with 10 ml of 10% aqueous sodium sulfite. Ethyl acetate is added, and the aqueous layer is extracted with ethyl acetate. The organic layers are combined and concentrated. The concentrate is purified by flash chromatography with 20:1 heptane-ethyl acetate to afford a red liquid. A second purification by flash chromatography affords 1.37 g (19% yield) of the title compound as a white solid, mp 42-45. The assay is % by NMR integration.

EXAMPLE 43

1-Cyclohexyloxy-4-benzoyloxy-2,2,6,6-tetramethylpiperidine

A mixture of 6.48 g (24.8 mmol) of 4-benzoyloxy-2,2,6,6-tetramethylpiperidine, $\frac{1}{100}^{th}$ of a solution of 0.270 g of anhydrous sodium carbonate diluted with water to a mass of 100 g (0.00270 g, 0.0254 mmol), and 37 ml of acetonitrile is heated to 80° C. A solution of 3.68 g (54 mmol) of 50% aqueous hydrogen peroxide is added to the reaction mixture over 1.75 hours while the temperature is brought to and maintained at reflux. After the peroxide is added, the reaction mixture is heated at 80° C. for 5 hours, then kept at room temperature overnight. A total of 0.60 g (5.9 mmol) of concentrated hydrochloric acid in 8 ml of water is added to the reaction mixture in portions. After the addition of 25 ml of cyclohexane to the reaction mixture, the temperature is brought to reflux (62° C.). A solution of 0.134 g (0.496 mmol) of ferric chloride hexahydrate in 2.5 ml of water is added to the reaction mixture. A solution of 6.96 g (102 mmol) of 50% aqueous peroxide is added dropwise over 3.25 hours to the reaction mixture while the temperature is maintained at 62° C. After the peroxide is added, the reaction mixture is stirred at reflux for 2 hours. Upon cooling, residual peroxide is decomposed by the addition of aqueous sodium sulfite solution. Work-up with ethyl acetate and purification by flash chromatography afford 3.06 g (34% overall yield) of the title compound. GC assay is 92%.

EXAMPLE 44

1-Cyclohexyloxy-2,2,6,6-tetramethylpiperidin-4-one

A mixture of 0.115 g (1.37 mmol) of sodium bicarbonate and 0.275 g (0.834 mmol) of sodium tungstate dihydrate in 2 mol of water is added to a mixture of 10.00 g (64.4 mmol) of 2,2,6,6-tetramethylpiperidin-4-one and 9 ml of acetonitrile at 300 C. A solution of 11.83 g (174 mmol) of 50% aqueous hydrogen peroxide is added dropwise to the reaction mixture over 4.25 hours while the reaction temperature is maintained at 30-35° C. Approximately 3.25 hours after the peroxide addition is begun, a mixture of 0.056 g of sodium bicarbonate and 0.134 g of sodium tungstate dihydrate in 1 ml of water is added to the reaction mixture. After a total reaction time of 6.5 hours, the reaction mixture is diluted with cyclohexane. The aqueous layer is extracted twice with a mixture of 2:1 cyclohexane-acetonitrile. The total amount of cyclohexane used is 60 ml. Acetonitrile (60 ml) is added to the combined organic layers. The reaction mixture is heated to 45° C. and a solution of 0.334 g (1.24 mmol) of ferrous chloride tetrahydrate and 0.312 g (5.20 mmol) of glacial acetic acid in 5 ml of water is added. A solution of 14.95 g (220 mmol) of 50% aqueous hydrogen peroxide is added dropwise to the reaction mixture over 4.25 hours as the reaction mixture is maintained at the reflux temperature of 60° C. The reaction mixture is cooled, and 10% aqueous sulfite solution is added to decompose excess peroxide. The aqueous layer is extracted with a 2:1 mixture of acetonitrile-cyclohexane and then with ethyl acetate. The combined organic layers are concentrated, and the concentrate is purified by flash chromatography with 100:7.5 heptane-ethyl acetate to afford 9.65 g (59% yield) of the title compound, a white solid, mp 33-37. GC assay is 99%.

EXAMPLE 44A

1-Cyclohexyloxy-2,2,6,6-tetramethylpiperidon-4-one

The procedure of Example 44 is repeated using an equivalent amount of ferric chloride hexahydrate in place of ferrous chloride tetrahydrate to give 9.51 g (58% yield) of the title compound. GC assay is 99%.

Examples 45A-B show the effect of reducing the total amount of solvent and cosolvent on the yield of product.

EXAMPLE 45A

1-Cyclohexyloxy-4-benzoyloxy-2,2,6,6-tetramethylpiperidine

The procedure of Example 31 is repeated using 20 ml of acetonitrile and 10 ml (approximately 5 equivalents) of cyclohexane to afford 4.99 g (77% yield) of the title compound. GC assay is 97%. Mass spectrometry and NMR analysis of the reaction product show no evidence for the presence of any product in which two N-oxyl moieties are bound to one molecule of cyclohexane. In Example 31, approximately 10 equivalents of cyclohexane are used, and the yield is 84%

EXAMPLE 45B

1-Cyclohexyloxy-4-benzoyloxy-2,2,6,6-tetramethylpiperidine

The procedure of Example 31 is repeated using 11 ml of acetonitrile and 5 ml (approximately 2.5 equivalents) of cyclohexane to afford 3.10 g (48% yield) of the title compound. GC assay is 93%.

Examples 46A-C demonstrate the use of a metal-ligand complex in the instant process.

EXAMPLE 46A

1-Cyclohexyloxy-4-benzoyloxy-2,2,6,6-tetramethylpiperidine

A suspension of 0.237 g (0.72 mmol) of ferrocenium hexafluorophosphate in 0.269 g (2.4 mmol) of trifluoroacetic acid and 3 ml of water is added to a mixture of 5.01 g (18.1 mmol) of 1-oxyl-4-benzoyloxy-2,2,6,6-tetramethylpiperidine, 25 ml of acetonitrile, and 16 ml of cyclohexane. The reaction mixture is heated to 50° C. A solution of 5.0 g (73 mmol) of 50% aqueous hydrogen peroxide is added dropwise over 2 hours to the reaction mixture while the temperature is brought to and maintained at 62° C. After the peroxide is added, the reaction mixture is heated at 62° C. for 30 minutes. The reaction mixture is cooled slowly to room temperature and stirred overnight. Peroxide is decomposed by the addition of aqueous sodium sulfite solution. Work-up with ethyl acetate and purification by flash chromatography afford 4.44 g (68% yield) of the title compound.

EXAMPLE 46B

1-Cyclohexyloxy-4-benzoyloxy-2,2,6,6-tetramethylpiperidine 2,2'-Dipyridyl (0.056 g, 0.36 mmol) is stirred with 28 ml of acetonitrile. To the acetonitrile solution is added a solution of 0.098 g (0.36 mmol) of ferric chloride hexahydrate in 2 ml of water. This purple mixture is stirred for 10 minutes prior to adding 19 ml of cyclohexane and 5.00 g (18.1 mmol) of 1-oxyl-4-benzoyloxy-2,2,6,6-tetramethylpiperidine. A solution of 3.84 g (69.5 mmol) of 50% aqueous hydrogen peroxide is added to the reaction mixture dropwise over 2.25 hours while the temperature is brought to and maintained at 62° C. After the peroxide is added, the reaction mixture is heated at reflux for 1 hour. The reaction mixture is cooled, and peroxide is decomposed by the addition of aqueous sodium sulfite solution. Ethyl acetate is added, and the organic layer is washed with water. The organic layer is concentrated, and the concentrate is purified by flash chromatography with 20:1 heptane-ethyl acetate to afford 4.82 g (74% yield) of the title compound. GC assay is 100%.

EXAMPLE 46C

1-Cyclohexyloxy-2,2,6,6-tetramethylpiperidin-4-ol

A solution of 0.404 g (1.1 mmol) of iron(II) ethylenediammonium sulfate tetrahydrate and 0.237 g (2.5 mmol) of methanesulfonic acid in 2 ml of water is added to a mixture of 5.00 g (29.0 mmol) of 1-oxyl-2,2,6,6-tetramethylpiperidin-4-ol, 38 ml of acetonitrile, and 24 ml of cyclohexane. The reaction mixture is heated to 50° C. A solution of 8.0 g (118 mmol) of 50% aqueous hydrogen peroxide is added to the reaction mixture dropwise over 4 hours while the temperature is brought to and maintained at reflux. After the peroxide is added, the reaction mixture is allowed to cool slowly to room temperature. The reaction mixture is stirred overnight at ambient temperature. The lower layer is discarded, and the organic layer is concentrated and purified by flash chromatography to afford 3.9 g (53% yield) of the title compound, a yellow solid. GC assay is greater than 99%.

EXAMPLE 47

1-Cyclohexyloxy-2,2,6,6-tetramethylpiperidin-4-one

The procedure of Example 30A is repeated with an equivalent amount of iron(III) citrate monohydrate used in place of ferrous chloride tetrahydrate. The yield is 1.57 g (34% yield) of the title compound. GC assay is greater than 99%.

EXAMPLE 48A

1-Octyloxy-4-benzoyloxy-2,2,6,6-tetramethylpiperidine

The procedure of Example 14L is repeated with copper(1) chloride in place of copper(II) chloride and octane in place of cyclohexane.

EXAMPLE 48B

1-Octyloxy-4-benzoyloxy-2,2,6,6-tetramethylpiperidine

The procedure of Example 14L is repeated with copper(1) chloride in place of copper(II) chloride and octane in place of cyclohexane. Hydrochloric acid is omitted from the reaction.

EXAMPLE 49

1-Cyclohexyloxy-4-benzoyloxy-2,2,6,6-tetramethylpiperidine

To a mixture of 5.00 g (18.1 mmol) of 1-oxyl-4-benzoyloxy-2,2,6,6-tetramethylpiperidine, 27 ml of acetonitrile, and 18 ml of cyclohexane is added 0.130 g (0.37 mmol) of iron (III) pivalate (iron (III) trimethylacetate). The reaction mixture is heated to 48° C. A solution of 5.05 g (74 mmol) of 50% aqueous hydrogen peroxide is added to the reaction mixture dropwise over 2.25 hours while the temperature is brought to and maintained at 62° C. After the peroxide is added, the reaction mixture is heated at 62° C. for 1.25 hours. The mixture is cooled slowly to room temperature. After the reaction mixture is allowed to stand overnight, excess peroxide is decomposed with aqueous sodium sulfite solution. Ethyl acetate is added, and the organic layer is concentrated. The concentrate is purified by flash chromatography with 20:1 heptane-ethyl acetate to afford 0.7 g (11% yield) of the title compound. GC assay is 99%.

Examples 50 and 51 show that in the absence of a suitable cosolvent, the reaction of an N-oxyl hindered amine with a hydrocarbon, a metal salt and hydrogen peroxide is ineffective, even if a small amount of phase transfer or emulsifying agent is added to the reaction mixture.

EXAMPLE 50

1-Cyclohexyloxy-2,2,6,6-tetramethylpiperidin-4-ol

A solution of 0.319 g (1.18 mmol) of ferric chloride hexahydrate and 0.337 g (3.4 mmol) of hydrochloric acid in 2 ml of water is added to a mixture of 5.01 g (29.1 mmol) of 1-oxyl-2,2,6,6-tetramethylpiperidin-4-ol, 0.134 g (0.3 mmol) of dioctyl sodium sulfosuccinate, 31 ml of cyclohexane, and 2 ml of water. The reaction mixture is heated to 52° C. A solution of 7.9 g (116 mmol) of 50% aqueous hydrogen peroxide is added to the reaction mixture dropwise over 3.5 hours while the temperature is brought to and maintained at 62-65° C. After the peroxide is added, the reaction mixture is heated at reflux for 45 minutes. The reaction mixture gives a negative test for hydrogen peroxide, and heating is discontinued. Work-up with ethyl acetate gives 0.055 g of a brown oil, which corresponds to less than 1% yield of the title compound if the oil has an assay of 100%. GC analysis does not show any 1-cyclohexyloxy-2,2,6,6-tetramethylpiperidin-4-ol present in the oil. By contrast, in Example 54G, a 76% yield of the title compound is obtained in the absence of a phase transfer or emulsifying agent when acetonitrile is used in combination with cyclohexane.

EXAMPLE 51

1-Cyclohexyloxy-2,2,6,6-tetramethylpiperidin-4-ol

A solution of 0.313 g (1.13 mmol) of ferrous sulfate heptahydrate and 0.327 g (3.4 mmol) of methanesulfonic acid in 10 ml of water is added to a mixture of 5.01 g (29.1 mmol) of 1-oxyl-2,2,6,6-tetramethylpiperidin-4-ol, 0.112 g (0.28 mmol, 1 mole percent) of tricaprylmethylammonium chloride (Aliquat® 336), and 31 ml of cyclohexane. The reaction mixture is heated to 55° C. A solution of 8.2 g (121 mmol) of 50% aqueous hydrogen peroxide is added to the reaction mixture dropwise over 3.5 hours while the temperature is brought to and maintained at 55-64° C. After the peroxide is added, the reaction mixture is heated at 62° C. for 20 minutes. The reaction mixture is cooled, and peroxide is decomposed with a small amount of aqueous sodium sulfite solution. Work-up with ethyl acetate and purification by flash chromatography give 0.04 g of an oil, which corresponds to a 0.5% yield of the title compound if the oil has an assay of 100%. GC analysis shows that the title compound comprises only 15% of the oil. By contrast, in Example 1, a 59% yield of the title compound is obtained with a solvent mixture of methanol and cyclohexane and 2 mol percent of a phase transfer agent. In Example 54, a 69% yield of the title compound is obtained with a solvent mixture of acetonitrile and cyclohexane in the absence of a phase transfer agent.

Example 52 illustrates that although acetonitrile is not inert under the conditions of the instant process, only a small amount of N-cyanomethoxy by-product is typically formed when a hydrocarbon solvent is present.

EXAMPLE 52

1-Cyclohexyloxy-2,2,6,6-tetramethylpiperidin-4-ol

At approximately one-hour intervals, an aliquot of the reaction mixture of Example 3 is removed and diluted with methanol. The aliquot is injected into a gas chromatograph, and peak areas are determined by an integrator. Although the solvent ratio is 1 part cyclohexane to 2 parts acetonitrile, based on volume, the ratio of the peak area of the 1-cyclohexyloxy title compound to the area of the corresponding acetonitrile product varies from 16:1 to 31:1. The amount of 1-cyanomethoxy-2,2,6,6-tetramethylpiperidin-4-ol in the final product is 4.6%.

EXAMPLE 53

1-Cyclohexyloxy-4-benzoyloxy-2,2,6,6-tetramethylpiperidine

A mixture of 0.061 g (0.294 mmol) of ruthenium(III) chloride hydrate and 0.047 g (0.783 mmol) of glacial acetic acid in 1.2 g of water is added to a mixture of 2.50 g (9.05 mmol) of 1-oxyl-4-benzoyloxy-2,2,6,6-tetraqmethylpiperidine, 12 ml of cyclohexane and 18 ml of acetonitrile that is heated to 50° C. The mixture is brought to reflux, and a solution of 3.54 g (52.0 mmol) of 50% aqueous hydrogen peroxide is added dropwise over 55 minutes. A mixture of 0.027 g of ruthenium (III) chloride hydrate and 0.041 g of glacial acetic acid in 0.5 g of water is added to the reaction mixture 40 minutes after the peroxide addition is begun. The reaction mixture is kept at reflux temperature for 1 hour after the peroxide is added.

The mixture is cooled to 40° and aqueous sodium sulfite is added to decompose residual peroxide. The aqueous layer is extracted with ethyl acetate, and the combined organic layers are concentrated. Purification of the concentrate by flash chromatography with a 100:6 mixture of heptane-ethyl acetate affords 0.14 g (4% yield) of the title compound, a colorless syrup. Structure is verified by NMR spectroscopy. GC assay is 99%.

EXAMPLE 54

1-Cyclohexyloxy-2,2,6,6-tetramethylpiperidin-4-ol

A solution of 0.234 g (0.842 mmol) of ferrous sulfate heptahydrate, 3 ml of water, and 0.293 g (3.05 mmol) of methanesulfonic acid is added to a mixture of 5.00 g (29.0 mmol) of 1-oxyl-2,2,6,6-tetramethylpiperidin-4-ol, 45 ml of acetonitrile, and 32 ml of cyclohexane, which has been heated to 62° C. A solution of 8.07 g (119 mmol) of 50% aqueous hydrogen peroxide is added dropwise over 2.25 hours to the reaction mixture while the temperature is maintained at reflux. A solution of 0.069 g of ferrous sulfate heptahydrate and 0.188 g of methanesulfonic acid in 2 ml of water is added to the reaction mixture 2 hours after the peroxide addition is started. A solution of 0.065 g of ferrous sulfate heptahydrate and 0.108 g of methanesulfonic acid in 1 ml of water is added to the reaction mixture 3.5 hours after the peroxide addition is started. After a total reaction time of 4.5 hours at reflux, the reaction mixture is allowed to cool. Excess peroxide is quenched with aqueous sodium sulfite solution. The aqueous layer is extracted with a 2:1 mixture of acetonitrile and cyclohexane, and the combined organic layers are washed with sodium hydroxide solution. To the organic layer are added 6 ml of t-butyl alcohol, 6 ml of water, 0.4 g of sodium hydroxide, and 0.70 g of sodium borohydride. The mixture is stirred for 3 hours, and the aqueous layer is extracted with ethyl acetate. The combined organic layers are washed with aqueous citric acid, aqueous sodium bicarbonate, and then concentrated. Purification by flash chromatography with 1:1 heptane-ethyl acetate affords 5.10 g (69% yield) of the title compound as a light yellow syrup, GC assay 93%.

EXAMPLE 54A

1-Cyclohexyloxy-2,2,6,6-tetramethylpiperidin-4-ol

The procedure of Example 54 is repeated using a nearly equivalent amount of concentrated hydrochloric acid in place of methanesulfonic acid. The yield of the title compound is 5.10 g (69%), GC assay 93%.

EXAMPLE 54B

1-Cyclohexyloxy-2,2,6,6-tetramethylpiperidin-4-ol

The procedure of Example 54 is repeated using a nearly equivalent amount of glacial acetic acid in place of methanesulfonic acid. The yield of the title compound is 5.31 g (72% yield), GC assay 93%.

EXAMPLE 54C

1-Cyclohexyloxy-2,2,6,6-tetramethylpiperidin-4-ol

The procedure of Example 54 is repeated using an equivalent amount of ferrous chloride tetrahydrate in place of ferrous sulfate heptahydrate. The yield of the title compound is 5.25 g (71% yield), GC assay 91%.

EXAMPLE 54D

1-Cyclohexyloxy-2,2,6,6-tetramethylpiperidin-4-ol

The procedure of Example 54 is repeated using a nearly equivalent amount of ferrous chloride tetrahydrate in place of ferrous sulfate heptahydrate and concentrated hydrochloric acid in place of methanesulfonic acid. The yield of the title compound is 5.45 g (74% yield), GC assay 95%.

EXAMPLE 54E

1-Cyclohexyloxy-2,2,6,6-tetramethylpiperidin-4-ol

The procedure of Example 54 is repeated using an equivalent amount of ferric chloride hexahydrate in place of ferrous sulfate heptahydrate. The yield of the title compound is 5.99 g (81% yield), GC assay 93%.

EXAMPLE 54F

1-Cyclohexyloxy-2,2,6,6-tetramethylpiperidin-4-ol

The procedure of Example 54 is repeated using an equivalent amount of ferric chloride hexahydrate in place of ferrous sulfate heptahydrate and a nearly equivalent amount of trifluoroacetic acid in place of methanesulfonic acid. The yield of the title compound is 5.10 g (69% yield), GC assay 93%.

EXAMPLE 54G

1-Cyclohexyloxy-2,2,6,6-tetramethylpiperidin-4-ol

The procedure of Example 54 is repeated using a nearly equivalent amount of ferric chloride hexahydrate in place of ferrous sulfate heptahydrate and concentrated hydrochloric acid in place of methanesulfonic acid. The yield of the title compound is 5.63 g (76% yield), GC assay 94%.

EXAMPLE 54H

1-Cyclohexyloxy-2,2,6,6-tetramethylpiperidin-4-ol

The procedure of Example 54 is repeated on twice the scale using a nearly equivalent amount of ferric sulfate hydrate in place of ferrous sulfate heptahydrate and 30% hydrogen peroxide solution in place of 50% hydrogen peroxide solution. The yield of the title compound is 9.63 g (65% yield), GC assay 85%.

EXAMPLE 54J

1-Cyclohexyloxy-2,2,6,6-tetramethylpiperidin-4-ol

Nanosized activated iron powder in mineral oil (0.042 g) is rinsed successively with two 2 ml portions of cyclohexane. Most of the solvent is removed with a pipette. The iron is added to a mixture of 5.00 g (29.0 mmol) of 1-oxyl-2,2,6,6- tetramethylpiperidin-4-ol, 44 ml of acetonitrile, and 32 ml of cyclohexane that has been heated to 40 degrees. To this mixture is carefully added over several minutes a solution of 0.548 g of concentrated hydrochloric acid in 3 ml of water. The reaction temperature is brought to reflux and a solution of 7.81 g (115 mmol) of 50% aqueous hydrogen peroxide is added dropwise over a period of 2.25 hours. After about one-half of the peroxide solution is added, a second portion of nanosized activated iron powder in mineral oil (0.039 g), rinsed twice with cyclohexane, and a solution of 0.166 g of concentrated hydrochloric acid in 1 ml of water are added to the reaction mixture. The reaction mixture is heated at 60-62 degrees for 1.5 hours after the peroxide has been added. After work up and purification according to the procedure of Example 54, the yield of the title compound is 5.53 g (75% yield), GC assay 96%.

EXAMPLE 54K

1-Cyclohexyloxy-2,2,6,6-tetramethylpiperidin-4-ol

Copper powder (0.060 g, 0.944 mmol) is added to a mixture of 5.00 g (29.0 mmol) of 1-oxyl-2,2,6,6-tetramethylpiperidin-4-ol, 44 ml of acetonitrile, and 30 ml of cyclohexane that has been heated to 40 degrees. A portion of a solution of 0.457 g of concentrated sulfuric acid in 3 mol of water is carefully added to the reaction mixture after the mixture is brought to reflux. To the refluxing reaction mixture is added dropwise over 2.5 hours a solution of 7.32 g (108 mmol) of 50% aqueous hydrogen peroxide. The remainder of the sulfuric acid solution is carefully added in portions to the reaction mixture during the first 15 minutes of the peroxide addition. After work up and purification according to the procedure of Example 54, the yield of the title compound is 5.22 g (70% yield), GC assay 94%.

EXAMPLE 54L

1-Cyclohexyloxy-2,2,6,6-tetramethylpiperidin-4-ol

Iron (II,III) oxide (0.107 g, 0.462 mmol) is added to a mixture of 2.51 g (14.6 mmol) of 1-oxyl-2,2,6,6-tetramethylpiperidin-4-ol, 24 ml of acetonitrile, and 15 ml of cyclohexane. The reaction mixture is brought to reflux, and a solution of 0.306 g of concentrated hydrochloric acid in 2 ml of water is added. A solution of 4.49 g (66 mmol) of 50% aqueous hydrogen peroxide is added dropwise over 70 minutes to the reaction mixture while the reaction temperature is maintained at 60-62 degrees. After approximately 65% of the peroxide is added, 0.055 g (0.238 mmol) of iron (II,III) oxide and a solution of 0.107 g of concentrated hydrochloric acid are added to the reaction mixture. The mixture is heated at reflux after the peroxide is added until GC analysis shows that the starting nitroxyl compound is no longer present. After work up and purification according to the procedure of Example 54, the yield of the title compound is 1.87 g (50% yield), GC assay 96%.

EXAMPLE 55

1-Cyclohexyloxy-2,2,6,6-tetramethylpiperidin-4-one

A solution of 0.369 g (1.86 mmol) of ferrous chloride tetrahydrate and 0.327 g (5.45 mmol) of glacial acetic acid in 6 ml of water is added to a mixture of 10.97 g (64.4 mmol) of 1-oxyl-2,2,6,6-tetramethylpiperidin-4-one, 100 ml of acetonitrile, and 65 ml of cyclohexane that is heated to 50° C. A solution of 18.21 g (268 mmol) of 50% aqueous hydrogen peroxide is added to the reaction mixture dropwise over 5.25 hours as the reaction temperature is brought to and maintained at 60-62° C. A total of 0.227 g of ferrous chloride tetrahydrate, 0.267 g of glacial acid, and 5 ml of water is added to the reaction mixture in 3 portions during the peroxide addition. Work up according to the procedure of Example 44 affords 10.83 g (66% yield) of the title compound, a white solid, mp 32-36. GC assay is 98.5%.

EXAMPLE 55A

1-Cyclohexyloxy-2,2,6,6-tetramethylpiperidin-4-one

When a comparable amount of ferric chloride hexahydrate is substituted for ferrous chloride tetrahydrate in the procedure of Example 55, the yield of the title compound is 9.63 g (59% yield, mp 33-36, GC assay 99%).

EXAMPLE 55B

1-Cyclohexyloxy-2,2,6,6-tetramethylpiperidin-4-one

1-Oxyl-2,2,6,6-tetramethylpiperidin-4-one (10.97 g, 64.4 mmol) is divided into 2 portions. A solution of 0.216 g (1.09 mmol) of ferrous chloride tetrahydrate and 0.185 9 (3.08 mmol) of glacial acetic acid in 3 ml of water is added to a mixture of 2 g of 1-oxyl-2,2,6,6-tetramethylpiperidin-4-one, 20 ml of acetonitrile, and 13 ml of cyclohexane that is heated to near reflux. A solution of 17.21 g (253 mmol) of 50% aqueous hydrogen peroxide is added to the reaction mixture dropwise over 4.75 hours as the reaction temperature is brought to and maintained at 60-62° C. As the peroxide is being added, a solution of the remaining portion of 1-oxyl-2,2,6,6-tetramethylpiperidin-4-one in 20 ml of acetonitrile is added to the reaction mixture dropwise over 3.5 hours. During the addition of the 1-oxyl compound, cyclohexane (47 ml) and acetonitrile (50 ml) are added to the reaction mixture in several portions. A total of 0.326 g of ferrous chloride tetrahydrate, 0.284 g of glacial acid, and 4 ml of water is added to the reaction mixture in 3 portions during the peroxide addition. Work up according to the procedure of Example 44 affords 10.31 g (63% yield) of the title compound. GC assay is 99%.

What is claimed is:

1. A process for preparing sterically hindered N-hydrocarbyloxyamines of formula Ia

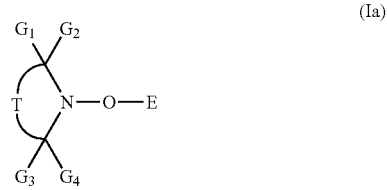

which process comprises
reacting a sterically hindered nitroxyl compound of formula IIa

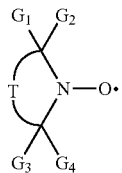
(IIa)

with a hydrocarbon containing no activated hydrogen atoms
in the presence of hydrogen peroxide, a catalytic amount of a peroxide decomposing transition metal, metal salt, metal oxide, or metal-ligand complex, and a relatively inert cosolvent selected from methanol and acetonitrile,
at a suitable temperature for a suitable time which brings about the desired conversion,
wherein $G_1$ through $G_4$ are each $C_1$-$C_4$ alkyl, or $G_1$ and $G_2$ together are pentamethylene, or $G_1$-$G_2$ together and $G_3$-$G_4$ together are each pentamethylene,
T is alkylene of 3 carbon atoms substituted by X,
X is hydrogen, hydroxyl, oxo, —NH—CO—R2, —O—CO—R2, or —NH—CO—NH—R2, where R2 is straight or branched alkyl of 1 to 18 carbon atoms, and
E is straight or branched $C_5$-$C_{18}$ alkyl, $C_5$-$C_{12}$ cycloalkyl, or $C_7$-$C_{12}$ bicycloalkyl or is $C_{10}$-$C_{20}$ aralkyl or aralkyl substituted by alkyl or aryl,
with the proviso that in the hydrocarbon, no carbon atom attached to an aromatic ring is substituted by hydrogen.

2. A process according to claim 1 for preparing sterically hindered N-hydrocarbyloxyamines of formula Ib

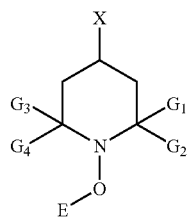
(Ib)

which process comprises
reacting a sterically hindered nitroxyl compound of formula IIb

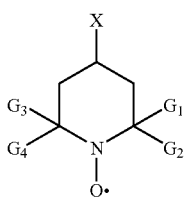
(IIb)

with a hydrocarbon containing no activated hydrogen atoms
in the presence of hydrogen peroxide, a catalytic amount of a peroxide decomposing transition metal salt, metal oxide, or metal-ligand complex, and a relatively inert cosolvent selected from methanol and acetonitrile,
at a suitable temperature for a suitable time which brings about the desired conversion,
wherein $G_1$ through $G_4$ are each $C_1$-$C_4$ alkyl, or $G_1$ and $G_2$ together are pentamethylene, or $G_1$-$G_2$ together are each pentamethylene,
X is hydrogen, hydroxyl, oxo, —NH—CO—R2, or —NH—CO—NH—R2, where R2 is straight or branched alkyl of 1 to 18 carbon atoms, and
E is straight or branched $C_5$-$C_{18}$ alkyl, $C_5$-$C_{12}$ cycloalkyl, or $C_7$-$C_{12}$ bicycloalkyl or is $C_{10}$-$C_{20}$ aralkyl or aralkyl substituted by alkyl or aryl, and
with the proviso that in the hydrocarbon from which E is derived, no carbon atom attached to an aromatic ring is substituted by hydrogen.

3. A process according to claim 1 for preparing sterically hindered N-hydrocarbyloxyamines of formula Ic

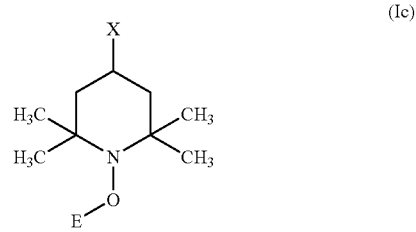
(Ic)

which process comprises
reacting a sterically hindered nitroxyl compound of formula IIc

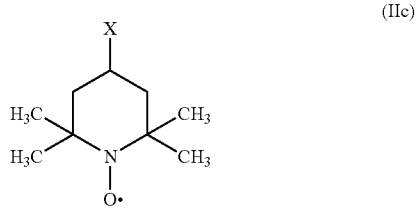
(IIc)

with a hydrocarbon containing no activated hydrogen atoms
in the presence of hydrogen peroxide, a catalytic amount of a peroxide decomposing transition metal salt, metal oxide, or metal-ligand complex, and a relatively inert cosolvent selected from methanol and acetonitrile,
at a suitable temperature for a suitable time which brings about the desired conversion,
where E is hexyl, heptyl, octyl, or cyclohexyl, and
X is hydrogen, hydroxyl, oxo, —O—CO—R2, wherein R2 is 1 to 8 carbon atoms.

4. A process according to claim 1 wherein the sterically hindered N-hydrocarbyloxyamine is
Bis(1-cyclohexyloxy-2,2,6,6-tetramethylpiperidin-4-yl) sebacate;
1-Cyclohexyloxy-4-methoxy-2,2,6,6-tetramethylpiperidine;
Bis(1-heptyloxy-2,2,6,6-tetramethylpiperidin-4-yl) sebacate;
1-Hexyloxy-4-methoxy-2,2,6,6-tetramethylpiperidine;
Bis[1-(2-methyl-2-phenylpropyloxy)-2,2,6,6-tetramethylpiperidin-4-yl] adipate;
1-(2-methyl-2-phenylpropyloxy)-4-benzoyloxy-2,2,6,6-tetramethylpiperidine;
2-Chloro-4,6-bis[N-(1-cyclohexyloxy-2,2,6,6-tetramethylpiperidin-4-yl)butylamino]-s-triazine;

2,4,6-Tris[N-(1-cyclohexyloxy-2,2,6,6-tetramethylpiperidin-4-yl)butylamino]-s-triazine;

Bis(1-octyloxy-2,2,6,6-tetramethylpiperidin-4-yl) sebacate;

1-Cyclooctyloxy-2,2,6,6-tetramethylpiperidin-4-ol;

Reaction product of bis(1-oxyl-2,2,6,6-tetramethylpiperidin-4-yl) sebacate and methylcyclohexane;

Reaction product of bis(1-oxyl-2,2,6,6-tetramethylpiperidin-4-yl) succinate and norbornane;

Reaction product of 1-oxyl-2,2,6,6-tetramethylpiperidin-4-ol and decahydronaphthalene;

Reaction product of bis(1-oxyl-2,2,6,6-tetramethylpiperidin-4-y) adipate and isooctane;

Reaction product of 1-oxyl-4-benzoyloxy-2,2,6,6-tetramethylpiperidine and isooctane;

Bis[1-(2,2-diphenylpropyloxy)-2,2,6,6-tetramethylpiperidin-4-yl] sebacate;

1-Cyclohexyloxy-2,2,6,6-tetramethylpiperidine;

Bis(1-octadecyloxy-2,2,6,6-tetramethylpiperidin-4-yl) succinate;

1-Cyclohexyloxy-4-octadecanoyloxy-2,2,6,6-tetramethylpiperidine;

1-Octyloxy-4-benzoyloxy-2,2,6,6-tetramethylpiperidine;

1-Cyclohexyloxy-4-benzoyloxy-2,2,6,6-tetramethylpiperidine;

1-Cyclohexyloxy-2,2,6,6-tetramethylpiperidin-4-ol; or

1-Cyclohexyloxy-2,2,6,6-tetramethylpiperidin-4-one.

5. A process according to claim 1 wherein the relatively inert cosolvent is acetonitrile.

6. A process according to claim 1 wherein the peroxide decomposing transition metal, metal salt or oxide is iron powder, nanosized activated iron powder, iron(II) chloride, iron(III) chloride, iron(III) acetylacetonate, iron(II) sulfate, iron(III) sulfate, iron(II) acetate, iron(II)oxide, iron(III)oxide, iron(II,III) oxide, iron(III) citrate, iron(II) oxalate, iron(III) oxalate, iron(III) nitrate, iron(II) perchlorate, iron(III) perchlorate, iron(II) trifluoroacetate, iron(II) tetrafluoroborate, iron(II) ethylenediammonium sulfate, iron(III) paratoluenesulfonate, ferrocenium hexafluorophosphate, ferrocenium tetrafluoroborate, copper powder, nanosized activated copper powder, copper(I) chloride, copper(II) chloride, copper (I) oxide, copper(II) oxide, copper(II) sulfate, copper(II) trifluoromethanesulfonate, or copper(II) trifluoroacetate.

7. A process according to claim 6 wherein the peroxide decomposing transition metal, metal salt or oxide is copper(I) chloride, copper(II) chloride, copper(II) sulfate, iron(II) chloride, iron(II) sulfate, iron(III) sulfate, iron(III) chloride, iron (II) oxide, iron (III) oxide, iron(II,III) oxide, copper(I) oxide, copper(II) oxide, copper powder, nanosized activated copper powder, iron powder, or nanosized activated iron powder.

8. A process according to claim 1 wherein the metal of the peroxide decomposing transition metal-ligand complex is vanadium(II), vanadium (III), tin(IV), copper(I), copper(II), titanium(III), titanium(IV), manganese(II), manganese(III), iron(II), iron(III), cerium (III), cobalt(II), or ruthenium(I).

9. A process according to claim 8 wherein the metal of the peroxide decomposing transition metal-ligand complex is iron(II) or iron (III).

10. A process according to claim 1 wherein the ligand of the peroxide decomposing transition metal-ligand complex is 2,2'-dipyridyl, 2,2':6,2''-terpyridine, 2,3-bis(2-pyridyl)pyrazine, 1,10-phenanthroline, ethylenediaminetetraacetic acid, ethylenediaminetetraacetic acid disodium salt, triphenylphosphine oxide, pyridine, picolinic acid, 2-pyrazinecarboxylic acid, diimines formed from the reaction of aniline or substituted anilines with 1,2-diketones, diimines such as N,N'-bis (salicylidene)ethylenediamine or N,N'-bis(3,5-di-tert-butylsalicylidene)-1,2-cyclohexanediamine, or cyclopentadiene.

11. A process according to claim 10 wherein the ligand of the peroxide decomposing transition metal-ligand complex is 2,2'-dipyridyl.

12. A process according to claim 1 where in the temperature is about 0 degrees to about 100 degrees Celsius.

13. A process according to claim 12 where in the temperature is about 20 degrees to about 100 degrees Celsius.

14. A process according to claim 13 where in the temperature is about 50 degrees to about 100 degrees Celsius.

15. A process according to claim 1 wherein additionally an acid is added.

16. A process according to claim 15 wherein the acid is hydrochloric acid, sulfuric acid, phosphoric acid, trifluoroacetic acid, tetrafluoroboric acid, acetic acid, boric acid, citric acid, or methanesulfonic acid.

17. A process according to claim 16 wherein the amount of acid is about 0.005 to about 1 mole per mole of N-oxyl moiety contained in the compound of formula (IIa).

18. A process according to claim 17 wherein the amount of acid is about 0.02 to about 0.25 moles of acid per mole of N-oxyl moiety contained in the compound of formula (IIa).

19. A process according to claim 1 wherein the amount of cosolvent is about 0.5 to about 2 parts by volume to 1 part hydrocarbon.

20. A process according to claim 1 wherein the amount of peroxide decomposing transition metal salt, metal oxide, or metal-ligand complex is about 0.001 to about 0.1 moles per mole of N-oxyl moiety.

21. A process according to claim 20 wherein the amount of peroxide decomposing transition metal salt, metal oxide, or metal-ligand complex is about 0.002 to about 0.05 moles per mole of N-oxyl moiety.

22. A process according to claim 1 wherein the amount of hydrocarbon is about 1 to about 15 moles of hydrocarbon per mole of N-oxyl moiety.

23. A process according to claim 22 wherein the amount of hydrocarbon is about 2 to about 10 moles of hydrocarbon per mole of N-oxyl moiety.

24. A process according to claim 23 wherein the amount of hydrocarbon is about 5 to about 10 moles of hydrocarbon per mole of N-oxyl moiety.

25. A process according to claim 1 wherein the amount of hydrogen peroxide is about 1 to about 10 moles per mole of N-oxyl moiety.

26. A process according to claim 25 wherein the amount of hydrogen peroxide is about 2 to about 5 moles per mole of N-oxyl moiety.

27. A process according to claim 1 wherein the concentration of hydrogen peroxide employed is about 15 to about 50% aqueous solution based on weight.

28. A process according to claim 27 wherein the concentration of hydrogen peroxide employed is about 30 to about 50% aqueous solution based on weight.

29. A process according to claim 28 wherein the concentration of hydrogen peroxide employed is about 50% aqueous solution based on weight.

* * * * *